US011767521B2

(12) United States Patent
Eng et al.

(10) Patent No.: US 11,767,521 B2
(45) Date of Patent: Sep. 26, 2023

(54) GENETICALLY MODIFIED BACTERIAL CELLS AND METHODS USEFUL FOR PRODUCING INDIGOIDINE

(71) Applicant: The Regents of the University of California, Oakland, CA (US)

(72) Inventors: Thomas T. Eng, Berkeley, CA (US); Deepanwita Banerjee, Emeryville, CA (US); Aindrila Mukhopadhyay, Oakland, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 17/180,633

(22) Filed: Feb. 19, 2021

(65) Prior Publication Data
US 2021/0332398 A1    Oct. 28, 2021

Related U.S. Application Data

(60) Provisional application No. 62/980,054, filed on Feb. 21, 2020.

(51) Int. Cl.
| | |
|---|---|
| *C12N 9/00* | (2006.01) |
| *C12N 9/12* | (2006.01) |
| *C12N 15/70* | (2006.01) |
| *C12N 15/78* | (2006.01) |
| *C12P 17/16* | (2006.01) |

(52) U.S. Cl.
CPC ............ *C12N 9/93* (2013.01); *C12N 9/1217* (2013.01); *C12N 15/70* (2013.01); *C12N 15/78* (2013.01); *C12P 17/165* (2013.01); *C12N 2310/20* (2017.05); *C12N 2510/02* (2013.01); *C12N 2511/00* (2013.01)

(58) Field of Classification Search
CPC ........ C12N 9/93; C12N 9/1217; C12P 17/165
See application file for complete search history.

(56) References Cited

U.S. PATENT DOCUMENTS

2019/0271020 A1*  9/2019  Thum ................... C12N 15/52

FOREIGN PATENT DOCUMENTS

CN        104535511        *  4/2015

OTHER PUBLICATIONS

English Tranlsation of CN 104535511. Retrieved on Sep. 20, 2022.*
Nikel. Pseudomonas putida as a functional chassis for industrial biocatalysis: from native biochemistry to trans-metabolism. Metabolic Engineering. 50. (2018) 142-15.*
Poblete-Castro. In-silico-driven metabolic engineering of Pseudomonas putida for enhanced production of poly-hydroxyalkanoates. Metabolic Engineering. 15 (2018). 113-123.*

(Continued)

*Primary Examiner* — Yong D Pak
(74) *Attorney, Agent, or Firm* — Robin C. Chiang; LAWRENCE BERKELEY NATIONAL LABORATORY

(57) ABSTRACT

The present invention provides for a genetically modified bacterial host cell capable of producing indigoidine, wherein the host cell comprises a non-ribosomal peptide synthetase (NRPS) that converts glutamine to indigoidine, and the bacterial host cell is reduced in its expression of one or more of the sixteen indicated enzymes.

18 Claims, 10 Drawing Sheets

Specification includes a Sequence Listing.

(56) References Cited

OTHER PUBLICATIONS

Pandhare et al., "Regulation and Function of Proline Oxidase under Nutrient Stress", 107 (4) 759-768 (2009).

Casini et al., "A pressure test to make 10 molecules in 90 days: external evaluation of methods to engineer biology." J. Am. Chem. Soc. 140, 4302-4316 (2018).

Wehrs et al., "Engineering Robust Production Microbes for Large-Scale Cultivation." Trends Microbiol. 27, 524-537 (2019).

Baral et al., "Techno-economic analysis and life-cycle greenhouse gas mitigation cost of five routes to bio-jet fuel blendstocks." Energy Environ. Sci. 12, 807-824 (2019).

Lievense, Scaling up Industrial Biotechnology. in (Life Science & Technology Programme of Delft University of Technology and Leiden University) at <https://www.genomatica.com/wp-content/uploads/2017/01/20160510-7th-Life-Sci-Symp-Lievense.pdf> (2016).

Delvigne, F., Takors, R., Mudde, R., van Gulik, W. & Noorman, H. Bioprocess scale-up/down as integrative enabling technology: from fluid mechanics to systems biology and beyond. Microb. Biotechnol. 10, 1267-1274 (2017).

Crater et al., "Scale-up of industrial microbial processes." FEMS Microbiol. Lett. 365, (2018).

Zahniser et al., The Growing Corn Economies of Mexico and the United States. (US Department of Agriculture, Economic Research Service). at <webpage for: ers.usda.gov/webdocs/publications/93542/ocs-19f-02.pdf?v=9932.1>.

OECD & Food and Agriculture Organization of the United Nations. OECD-FAO Agricultural Outlook 2018-2027. (OECD, 2018). doi:10.1787/agr_outlook-2018-en.

Newsome, A. G., Culver, C. A. & van Breemen, R. B. Nature's palette: the search for natural blue colorants. J. Agric. Food Chem. 62, 6498-6511 (2014).

Bloudoff et al., "Structural and functional aspects of the nonribosomal peptide synthetase condensation domain superfamily: discovery, dissection and diversity." Biochim. Biophys. Acta Proteins Proteom. 1865, 1587-1604 (2017).

Nogales et al., "High-quality genome-scale metabolic modeling of Pseudomonas putida highlights its broad metabolic capabilities." Environ. Microbiol. (2019).

Hädicke et al., "Computing complex metabolic intervention strategies using constrained minimal cut sets." Metab. Eng. 13, 204-213 (2011).

Von Kamp et al., "Growth-coupled overproduction is feasible for almost all metabolites in five major production organisms." Nat. Commun. 8, 15956 (2017).

Thompson et al., "Massively Parallel Fitness Profiling Reveals Multiple Novel Enzymes in Pseudomonas putida Lysine Metabolism." MBio 10, (2019).

Price et al., "Mutant phenotypes for thousands of bacterial genes of unknown function." Nature 557, 503-509 (2018).

Ajikumar et al., "Isoprenoid pathway optimization for Taxol precursor overproduction in Escherichia coli." Science 330, 70-74 (2010).

Dunlop et al., "Engineering microbial biofuel tolerance and export using efflux pumps." Mol. Syst. Biol. 7, 487 (2011).

Weickert et al., "The galactose regulon of Escherichia coli." Mol. Microbiol. 10, 245-251 (1993).

Holden et al., "Structure and function of enzymes of the Leloir pathway for galactose metabolism." J. Biol. Chem. 278, 43885-43888 (2003).

Takahashi et al., "Cloning and characterization of a Streptomyces single module type non-ribosomal peptide synthetase catalyzing a blue pigment synthesis." J. Biol. Chem. 282, 9073-9081 (2007).

Verstrepen et al., "Intragenic tandem repeats generate functional variability." Nat. Genet. 37, 986-990 (2005).

Bzymek et al., "Instability of repetitive DNA sequences: the role of replication in multiple mechanisms." Proc Natl Acad Sci USA 98, 8319-8325 (2001).

Reis et al., "Simultaneous repression of multiple bacterial genes using nonrepetitive extra-long sgRNA arrays." Nat. Biotechnol. 37, 1294-1301 (2019).

Barrangou et al., "CRISPR provides acquired resistance against viruses in prokaryotes." Science 315, 1709-1712 (2007).

Straight et al., "GFP tagging of budding yeast chromosomes reveals that protein-protein interactions can mediate sister chromatid cohesion." Curr. Biol. 6, 1599-1608 (1996).

Zetsche et al., Cpf1 is a single RNA-guided endonuclease of a class 2 CRISPR-Cas system. Cell 163, 759-771 (2015).

Mehrer et al., Growth-coupled bioconversion of levulinic acid to butanone. Metab. Eng. 55, 92-101 (2019).

Lo et al., "A Two-Layer Gene Circuit for Decoupling Cell Growth from Metabolite Production." Cell Syst. 3, 133-143 (2016).

Alter et al., "Determination of growth-coupling strategies and their underlying principles." BMC Bioinformatics 20, 447 (2019).

Klamt et al., "On the feasibility of growth-coupled product synthesis in microbial strains." Metab. Eng. 30, 166-178 (2015).

Yim et al., "Metabolic engineering of Escherichia coli for direct production of 1,4-butanediol." Nat. Chem. Biol. 7, 445-452 (2011).

Shen et al., "Driving forces enable high-titer anaerobic 1-butanol synthesis in Escherichia coli." Appl. Environ. Microbiol. 77, 2905-2915 (2011).

Lan et al., "ATP drives direct photosynthetic production of 1-butanol in cyanobacteria." Proc Natl Acad Sci USA 109, 6018-6023 (2012).

Wang et al., "Developing a pyruvate-driven metabolic scenario for growth-coupled microbial production." Metab. Eng. 55, 191-200 (2019).

Shabestary et al., "Computational metabolic engineering strategies for growth-coupled biofuel production by Synechocystis." Metab. Eng. Commun. 3, 216-226 (2016).

Von Kamp et al., "Enumeration of smallest intervention strategies in genome-scale metabolic networks." PLoS Comput. Biol. 10, e1003378 (2014).

Xu et al., "Efficient production of indigoidine in Escherichia coli." J. Ind. Microbiol. Biotechnol. 42, 1149-1155 (2015).

Wehrs et al., "Production efficiency of the bacterial non-ribosomal peptide indigoidine relies on the respiratory metabolic state in S. cerevisiae." Microb. Cell Fact. 17, 193 (2018).

Wehrs et al., "Sustainable bioproduction of the blue pigment indigoidine: Expanding the range of heterologous products in R. toruloides to include non-ribosomal peptides." Green Chem. (2019). doi:10.1039/C9GC00920E.

Mukhopadhyay, "Tolerance engineering in bacteria for the production of advanced biofuels and chemicals." Trends Microbiol. 23, 498-508 (2015).

George et al., "Isoprenoid drugs, biofuels, and chemicals—artemisinin, farnesene, and beyond." Adv. Biochem. Eng. Biotechnol. 148, 355-389 (2015).

Withers et al., "Identification of isopentenol biosynthetic genes from Bacillus subtilis by a screening method based on isoprenoid precursor toxicity." Appl. Environ. Microbiol. 73, 6277-6283 (2007).

Klamt et al., "Structural and functional analysis of cellular networks with CellNetAnalyzer." BMC Syst. Biol. 1, 2 (2007).

Heirendt et al., Creation and analysis of biochemical constraint-based models using the COBRA Toolbox v.3.0. Nat. Protoc. 14, 639-702 (2019).

Salvachúa et al., "Towards lignin consolidated bioprocessing: simultaneous lignin depolymerization and product generation by bacteria." Green Chem. 17, 4951-4967 (2015).

Rio et al., "Purification of RNA using TRIzol (TRI reagent)." Cold Spring Harb. Protoc. 2010, pdb.prot5439 (2010).

Eng et al., "Restoration of biofuel production levels and increased tolerance under ionic liquid stress is enabled by a mutation in the essential Escherichia coli gene cydC." Microb. Cell Fact. 17, 159 (2018).

Nogales et al., "Expanding the computable reactome in Pseudomonas putida reveals metabolic cycles providing robustness", bioRxiv (bioRxiv 139121; doi: https://doi.org/10.1101/139121) (2017).

International Search Report and Written Opinion of PCT/US21/19112, dated May 13, 2021, 11 pages.

(56) References Cited

OTHER PUBLICATIONS

Banerjee et al., "Genome-scale metabolic rewiring improves titers rates and yields of the non-native product indgoidine at scale", Nature Communications, 11: 5385 (2020).

* cited by examiner

SEQUENCE LISTING

<160> NUMBER OF SEQ ID NOS: 4

<210> SEQ ID NO 1
<211> LENGTH: 1283
<212> TYPE: PRT
<213> ORGANISM: Streptomyces lavendulae

<400> SEQUENCE: 1

```
Met Thr Leu Gln Glu Thr Ser Val Leu Glu Pro Thr Leu Arg Gly Thr
1               5                   10                  15

Thr Thr Leu Pro Asp Leu Leu Ala Lys Arg Val Ala Glu His Pro Glu
            20                  25                  30

Ala Thr Ala Val Ala Tyr Arg Asp Glu Lys Leu Thr Tyr Arg Glu Leu
        35                  40                  45

Ala Ser Arg Ser Ser Ala Leu Ala Glu Tyr Leu Arg His Leu Gly Val
    50                  55                  60

Ser Thr Asp Asp Cys Val Gly Leu Phe Val Glu Pro Ser Ile Asp Leu
65                  70                  75                  80

Met Val Gly Ala Trp Gly Ile Leu Ser Ala Gly Ala Ala Tyr Leu Pro
                85                  90                  95

Leu Ser Pro Glu Tyr Pro Glu Asp Arg Leu Arg Tyr Met Ile Glu Asn
            100                 105                 110

Ser Gln Ala Lys Ile Ile Leu Ala Gln Gln Arg Leu Val Thr Arg Leu
        115                 120                 125

Arg Glu Leu Ala Pro Gln Asp Val Arg Val Thr Leu Arg Glu Ser
    130                 135                 140

Glu Ala Phe Val Leu Pro Glu Gly Gln Val Ala Pro Ile Glu Gly
145                 150                 155                 160

Ala Arg Pro Asp Ser Leu Ala Tyr Val Ile Tyr Thr Ser Gly Ser Thr
                165                 170                 175

Gly Lys Pro Lys Gly Val Met Ile Glu His His Ser Ile Val Ser Gln
            180                 185                 190

Leu Gly Trp Leu Arg Glu Thr Tyr Gly Ile Asp Arg Ser Lys Thr Ile
        195                 200                 205

Leu Gln Lys Thr Pro Met Ser Phe Asp Ala Ala Gln Trp Glu Ile Leu
    210                 215                 220

Ser Pro Ala Asn Gly Ala Thr Val Val Met Gly Ala Pro Gly Val Tyr
225                 230                 235                 240

Ala Asp Pro Glu Gly Leu Ile Glu Thr Ile Val Lys Tyr Gly Val Thr
                245                 250                 255

Thr Leu Gln Cys Val Pro Thr Leu Leu Gln Gly Leu Leu Asp Thr Glu
            260                 265                 270

Lys Phe Pro Glu Cys Thr Ser Leu Gln Gln Ile Phe Ser Gly Gly Glu
        275                 280                 285

Ala Leu Ser Arg Leu Leu Ala Ile Gln Thr Thr Gln Glu Met Pro Gly
    290                 295                 300

Arg Ala Leu Ile Asn Val Tyr Gly Pro Thr Glu Cys Thr Ile Asn Ser
305                 310                 315                 320

Ser Ser Tyr Ala Val Asp Pro Ala Glu Leu Gly Glu Ala Pro Gln Ser
                325                 330                 335

Ile Ser Ile Gly Ala Pro Val Ala Asp Thr Glu Tyr His Ile Leu Gly
            340                 345                 350

Lys Glu Asp Leu Lys Pro Val Gly Val Gly Glu Ile Gly Glu Leu Tyr
        355                 360                 365
```

-continued

```
Ile Gly Gly Gln Leu Ala Arg Gly Tyr Leu His Arg Pro Asp Leu
370             375             380

Thr Ala Glu Arg Phe Leu Glu Ile Glu Val Thr Glu Gly Ala Gly Pro
385                 390             395                 400

Val Arg Leu Tyr Lys Thr Gly Asp Leu Gly Gln Trp Asn Pro Asp Gly
            405             410                 415

Thr Val Gln Phe Ala Gly Arg Ala Asp Asn Gln Val Lys Leu Arg Gly
            420             425             430

Tyr Arg Val Glu Leu Asp Glu Ile Ser Leu Ala Ile Glu Asn His Asp
            435             440             445

Trp Val Arg Asn Ala Ala Val Ile Val Lys Asn Asp Gly Arg Thr Gly
450                 455             460

Phe Gln Asn Leu Ile Ala Cys Val Glu Leu Ser Glu Lys Glu Ala Ala
465                 470             475                 480

Leu Met Asp Gln Gly Asn His Gly Ser His His Ala Ser Lys Lys Ser
                485             490             495

Lys Leu Gln Val Lys Ala Gln Leu Ser Asn Pro Gly Leu Arg Asp Asp
            500             505             510

Ala Asp Leu Ala Ala Arg Val Ala Tyr Asp Leu Pro Gly Ala Glu Pro
            515             520             525

Thr Pro Glu Gln Arg Ser Arg Val Phe Ala Arg Lys Thr Tyr Arg Phe
530                 535             540

Tyr Glu Gly Gly Ala Val Thr Glu Ala Asp Leu Leu Ala Leu Leu Gly
545                 550             555                 560

Gly Gln Val Pro Ala Ala Tyr Ser Arg Lys Ala Ala Asp Leu Ala Pro
                565             570             575

Ala Glu Leu Gly Gln Ile Leu Arg Trp Phe Gly Gln Tyr Leu Ser Glu
            580             585             590

Glu Arg Leu Leu Pro Lys Tyr Gly Tyr Ala Ser Pro Gly Ala Leu Tyr
            595             600             605

Ala Thr Gln Leu Tyr Phe Glu Leu Glu Gly Val Gly Gly Leu Gln Pro
            610             615             620

Gly Tyr Tyr Tyr Gln Pro Gln Arg His Gln Leu Val Leu Ile Ser
625                 630             635             640

Glu Lys Ala Ala Thr Gly Arg Pro Thr Ala His Ile His Phe Ile Gly
                645             650             655

Lys Arg Gly Gly Ile Glu Pro Val Tyr Lys Asn Asn Ile Gln Glu Val
                660             665             670

Leu Glu Ile Glu Thr Gly His Ile Val Gly Leu Phe Glu Gln Val Leu
            675             680             685

Pro Ala Tyr Gly Leu Asp Ile Arg Asp Leu Ala Tyr Glu Pro Ala Val
690                 695             700

Arg Asp Leu Leu Asp Val Pro Glu Glu Asp Phe Tyr Leu Gly Thr Phe
705                 710             715                 720

Glu Leu Val Pro His Thr Gly Arg Arg Glu Asp His Ala Glu Val Tyr
                725             730             735

Val Gln Thr His Gly Ser Lys Val Ala Asn Leu Pro Glu Gly Gln Tyr
            740             745             750

Arg Tyr Ala Asp Gly Thr Leu Thr Arg Phe Ser Asp Asp Ile Val Leu
            755             760             765

Lys Lys Gln Val Ile Ala Ile Asn Gln Ser Val Tyr Gln Ala Ala Ser
770                 775             780

Phe Gly Ile Ser Val Ile Ser Arg Ala Pro Glu Glu Trp Met His Tyr
```

-continued

```
            785                 790                 795                 800
Val Thr Leu Gly Lys Lys Leu Gln His Leu Met Met Asn Gly Leu Gly
                    805                 810                 815
Leu Gly Phe Met Ser Ser Gly Tyr Ser Ser Lys Thr Gly Asn Pro Leu
                820                 825                 830
Pro Ala Ser Arg Arg Ile Asp Ser Val Leu Gln Ala Asn Gly Val Glu
                835                 840                 845
Ser Gly Pro Ser Tyr Phe Phe Val Gly Arg Val Ser Asp Glu Gln
            850                 855                 860
Leu Gly His Glu Gly Met Arg Glu Asp Ser Val His Met Arg Gly Pro
865                 870                 875                 880
Ala Glu Leu Ile Arg Asp Asp Leu Val Ser Phe Leu Pro Asp Tyr Met
                885                 890                 895
Ile Pro Asn Arg Val Val Val Phe Glu Arg Leu Pro Leu Ser Ala Asn
                900                 905                 910
Gly Lys Ile Asp Ala Lys Ala Leu Ala Ala Ser Asp Gln Val Asn Ala
            915                 920                 925
Glu Leu Val Glu Arg Pro Phe Val Ala Pro Arg Thr Glu Thr Glu Lys
        930                 935                 940
Glu Ile Ala Glu Val Trp Ala Lys Ser Leu Arg Arg Glu Ser Val Ser
945                 950                 955                 960
Val Gln Asp Asp Phe Phe Glu Ser Gly Gly Asn Ser Leu Ile Ala Val
                965                 970                 975
Gly Leu Ile Arg Glu Leu Asn Ser Arg Leu Gly Val Ser Leu Pro Leu
            980                 985                 990
Gln Ser Val Leu Glu Ser Pro Thr  Val Glu Lys Leu Ser  Arg Arg Leu
        995                 1000                1005
Glu Arg  Glu Val Ala Gln Glu  Ser Ser Arg Leu Val  Arg Leu His
    1010                1015                1020
Ala Glu  Thr Gly Lys Asp Arg  Pro Val Leu Cys Trp  Pro Gly Leu
    1025                1030                1035
Gly Gly  Tyr Pro Met Asn Leu  Arg Thr Leu Ala Gly  Glu Ile Gly
    1040                1045                1050
Leu Gly Arg Ser Phe Tyr Gly  Ile Gln Ala His Gly  Ile Asn Glu
    1055                1060                1065
Gly Glu  Ala Pro Tyr Ala Thr  Ile Thr Glu Met Ala  Lys Ala Asp
    1070                1075                1080
Ile Glu  Ala Ile Lys Glu Leu  Gln Pro Lys Gly Pro  Tyr Thr Leu
    1085                1090                1095
Trp Gly  Tyr Ser Phe Gly Ala  Arg Val Ala Phe Glu  Thr Ala Tyr
    1100                1105                1110
Gln Leu  Glu Gln Ala Gly Glu  Lys Val Asp Asn Leu  Phe Leu Ile
    1115                1120                1125
Ala Pro  Gly Ser Pro Thr Val  Arg Ala Glu Asn Gly  Lys Val Tyr
    1130                1135                1140
Gly Arg  Glu Ala Ser Phe Ala  Asn Arg Ala Tyr Thr  Thr Ile Leu
    1145                1150                1155
Phe Ser  Val Phe Thr Gly Thr  Ile Ser Gly Pro Asp  Leu Glu Lys
    1160                1165                1170
Cys Leu  Glu Ser Ala Thr Asp  Glu Glu Ser Phe Ala  Gly Phe Ile
    1175                1180                1185
Ser Glu  Leu Lys Gly Ile Asp  Val Asp Leu Ala Lys  Arg Ile Ile
    1190                1195                1200
```

```
Ser Val Val Gly Gln Thr Tyr Glu Phe Glu Tyr Ser Phe Arg Glu
    1205                1210                1215

Leu Ala Glu Arg Thr Leu Ala Ala Pro Val Thr Ile Phe Lys Ala
    1220                1225                1230

Arg Gly Asp Asp Tyr Ser Phe Ile Glu Asn Ser Asn Gly Tyr Ser
    1235                1240                1245

Ala Glu Pro Pro Thr Val Ile Asp Leu Asp Ala Asp His Tyr Ser
    1250                1255                1260

Leu Leu Arg Thr Pro Asp Ile Gly Glu Leu Val Lys His Ile Arg
    1265                1270                1275

Tyr Leu Leu Gly Glu
    1280

<210> SEQ ID NO 2
<211> LENGTH: 76
<212> TYPE: PRT
<213> ORGANISM: Streptomyces lavendulae

<400> SEQUENCE: 2

Ala Pro Arg Thr Glu Thr Glu Lys Glu Ile Ala Glu Val Trp Ala Lys
1               5                   10                  15

Ser Leu Arg Arg Glu Ser Val Ser Val Gln Asp Asp Phe Phe Glu Ser
                20                  25                  30

Gly Gly Asn Ser Leu Ile Ala Val Gly Leu Ile Arg Glu Leu Asn Ser
            35                  40                  45

Arg Leu Gly Val Ser Leu Pro Leu Gln Ser Val Leu Glu Ser Pro Thr
        50                  55                  60

Val Glu Lys Leu Ser Arg Arg Leu Glu Arg Glu Val
65                  70                  75

<210> SEQ ID NO 3
<211> LENGTH: 8
<212> TYPE: PRT
<213> ORGANISM: Streptomyces lavendulae

<400> SEQUENCE: 3

Ser Arg Arg Leu Glu Arg Glu Val
1               5

<210> SEQ ID NO 4
<211> LENGTH: 21
<212> TYPE: PRT
<213> ORGANISM: Streptomyces lavendulae

<400> SEQUENCE: 4

Ser Arg Arg Leu Glu Arg Glu Val Ala Gln Glu Ser Ser Arg Leu Val
1               5                   10                  15

Arg Leu His Ala Glu
            20
```

GENETICALLY MODIFIED BACTERIAL CELLS AND METHODS USEFUL FOR PRODUCING INDIGOIDINE

CROSS REFERENCE TO RELATED APPLICATIONS

This application claims priority to U.S. Provisional Patent Application Ser. No. 62/980,054, filed Feb. 21, 2020, which is incorporated by reference in its entirety.

STATEMENT OF GOVERNMENTAL SUPPORT

The invention was made with government support under Contract Nos. DE-AC02-05CH11231 awarded by the U.S. Department of Energy. The government has certain rights in the invention.

FIELD OF THE INVENTION

The present invention is in the field of the production of indigoidine.

REFERENCE TO A "SEQUENCE LISTING" SUBMITTED AS ASCII TEXT FILES VIA EFS-WEB

The Sequence Listing written in file 2019-145-02_Sequence_Listing_ST25.txt created on Feb. 19, 2021, 12,697 bytes, machine format IBM-PC, MS-Windows operating system, in accordance with 37 C.F.R. §§ 1.821- to 1.825, is hereby incorporated by reference in its entirety for all purposes.

BACKGROUND OF THE INVENTION

Heterologous production of bioproducts has been demonstrated for a very large number of compounds and in a wide variety of microbial hosts[1,2]. Yet, even the most well-designed heterologous pathway requires considerable additional work to reach production titers rates and yields (TRY) necessary for the adoption of these systems in the industry[3,4]. In addition, the production parameters of a strain at lab-scale is often not predictive of its performance and robustness when cultivated in different modes or higher scales, and several approaches from a practical or process engineering standpoint have been described[5,6]. These issues could be attributed to the intrinsic competition for carbon between the native metabolism and the heterologous pathway, leading to phenotypic drift in diverse growth modes. As a result, only a small fraction of bioproduction strains have been successfully scaled and deployed[2].

Indigoidine is a natural blue pigment natively produced by several bacteria via biosynthetic gene clusters. This 3',3'-bipyridyl pigment is formed through condensation of two molecules of L-glutamine catalyzed by a non-ribosomal peptide synthetase (NRPS). NRPS are large assembly-line enzymes and are organized in modules that are each responsible for the introduction of one L-amino acid to the NRP. Each module consists of several domains with defined functions that synthesize NRPs in a sequential multi-step process. The secondary metabolite class of NRPs includes molecules with a range of pharmaceutical applications, such as immunosuppressants, antibiotics, anticancer drugs and antiviral compounds. However, the low NRP production levels from native hosts and their complex chemical structures impede mass production by purification from biological material or chemical synthesis. Furthermore, despite the availability of biosynthetic tools for metabolic engineering and pathway discovery, optimization of NRP production in their natural hosts remains challenging.

SUMMARY OF THE INVENTION

The present invention provides for a genetically modified bacterial host cell capable of producing indigoidine, wherein the host cell comprises a non-ribosomal peptide synthetase (NRPS) that converts glutamine to indigoidine, and the bacterial host cell is reduced in its expression of one or more of the following enzymes or enzymes catalyzing the indicated reactions: Glucose dehydrogenase (ubiquinone 8 as acceptor, periplasm); Phosphoenolpyruvate synthase; Malate dehydrogenase; Malate dehydrogenase (ubiquinone 8 as acceptor); Malic enzyme NADP; Transaldolase; N acetylornithine deacetylase; Ornithine Decarboxylase; Proline dehydrogenase; Poly 3 hydroxyalkanoate polymerase 3 Hydroxybutanoyl CoA; 1,6 anhydrous N Acetylmuramate kinase; D lactate transport via proton symport periplasm; Carboxylic acid dissociation; and HCO3 equilibration reaction, and any other described in Table 4, and any other genes described in Supplemental Tables 5 and 6 of U.S. Provisional Patent Application Ser. No. 62/980,054, filed Feb. 21, 2020, which is incorporated by reference in its entirety.

In some embodiments, the bacterial host cell is a proteobacteria cell. In some embodiments, the proteobacteria cell is a Gammaproteobacteria cell. In some embodiments, the Gammaproteobacteria cell is a Pseudomonadales or Enterobacterales cell. In some embodiments, the Gammaproteobacteria cell is a Pseudomonadales cell, which is a Pseudomonadaceae cell. In some embodiments, the Pseudomonadaceae cell is a *Pseudomonas, Azotobacter, Mesophilobacter, Oblitimonas, Permianibacter, Rugamonas,* or *Thiopseudomonas* cell. In some embodiments, the *Pseudomonas* cell is a *P. putida, P. aeruginosa, P. chlororaphis, P. fluorescens, P. pertucinogena, P. stutzeri, P. syringae, P. cremoricolorata, P. entomophila, P. fulva, P. monteilii, P. mosselii, P. oryzihabitans, P. parafluva,* or *P. plecoglossicida*. In some embodiments, the Gammaproteobacteria cell is a Enterobacterales cell, which is a Enterobacteriaceae cell. In some embodiments, the Enterobacteriaceae cell is an *Escherichia, Enterobacillus, Enterobacter, Klebsiella, Salmonella,* or *Shigella* cell. In some embodiments, the *Escherichia* cell is an *E. coli, E. albertii, E. fergusonii, E. hermanii, E. marmotae,* or *E. vulneris*. In some embodiments, the host cell is a Gram negative bacterium. In some embodiments, the host cell is a bacterium from the *Azotobacter, Escherichia, Salmonella, Vibrio, Pasteurella, Haemophilus,* or *Pseudomonas* genus. In some embodiments, the host cell is a bacterium from the species *Escherichia coli, Salmonella enterica, Vibrio cholerae, Pasteurella multocida, Haemophilus influenza, Pseudomonas putida,* or *Pseudomonas aeruginosa*.

In some embodiments, the bacterial host cell in its unmodified state in nature comprises one or more genes encoding the following enzymes or enzymes catalyzing the indicated reactions: Glucose dehydrogenase (ubiquinone 8 as acceptor, periplasm); Phosphoenolpyruvate synthase; Malate dehydrogenase; Malate dehydrogenase (ubiquinone 8 as acceptor); Malic enzyme NADP; Transaldolase; N acetylornithine deacetylase; Ornithine Decarboxylase; Proline dehydrogenase; Poly 3 hydroxyalkanoate polymerase 3 Hydroxybutanoyl CoA; 1,6 anhydrous N Acetylmuramate kinase; D lactate transport via proton symport periplasm; Carboxylic acid dissociation; and HCO3 equilibration reaction. In some embodiments, the bacterial host cell in its unmodified state in nature comprises two or more, three or more, four or more, five or more, six of more, seven or more, eight or more, nine or more, ten or more, eleven or more, twelve or more, thirteen or more, fourteen or more, fifteen or more, or all of the genes described herein.

In some embodiments, the NRPS is heterologous to the host cell. In some embodiments, the NRPS is a bacterial NRPS. In some embodiments, the NRPS is a *Streptomyces lavendulae* NRPS (BpsA).

In some embodiments, the genetically modified bacterial host cell is reduced in its expression of two or more, three or more, four or more, five or more, six of more, seven or more, eight or more, nine or more, ten or more, eleven or more, twelve or more, thirteen or more, fourteen or more, fifteen or more, or all of the enzymes or enzymes catalyzing the indicated reaction indicated herein.

In some embodiments, the reduced in its expression of one or more of the following enzymes or enzymes catalyzing the indicated reactions includes, but is not limited to, reduced transcription of a gene by any suitable means (such as gene silencing, antisense, replacement of a native promoter with a promoter with a lower transcription rate, introduction of one or more repressor sites, replacement or elimination of an activation site, or the like), reduced translation of the transcript of a gene by any suitable means (such as an altered ribosomal binding site that has a reduced ability to bind to a ribosome), or the deletion of a part of all of the native promoter, or the deletion of a part of all of the open reading frame of the gene, or any means taught herein. Gene silencing includes RNAi, CRISPR, or siRNA. The reduction of transcription, translation, and/or gene expression can be about 10%, 20%, 30%, 40%, 50%, 60%, 70%, 80%, 90%, or 100%, or any range of value between any two preceding values, including the stated values.

The present invention provides for a method for a genetically modified bacterial host cell producing indigoidine, comprising (a) providing a genetically modified bacterial host cell of the present invention, (b) culturing or growing the host cell in a suitable culture or medium such that indigoidine is produced, and (c) optionally extracting or separating the indigoidine from the rest of the culture or medium, and/or host cell.

In some embodiments, the providing step (a) comprises introducing a nucleic acid encoding the NRPS operatively linked to a promoter capable of expressing the NRPS in the host cell into the host cell. In some embodiments, the culturing or growing step (b) comprises the host cell growing by respiratory cell growth. In some embodiments, the culturing or growing step (b) takes place in a batch process or a fed-batch process, such as a high-gravity fed-batch process. In some embodiments, the culture or medium comprises hydrolysates derived or obtained from a biomass, such as a lignocellulosic biomass. In some embodiments, the culture or medium comprises one or more carbon sources, such as a sugar, such as glucose or galactose, or glycerol, or a mixture thereof. In some embodiments, the carbon source is fermentable. In some embodiments, the carbon source is non-fermentable. In some embodiments, the culture or medium comprises urea as a nitrogen course.

The present invention provides for a method for constructing a genetically modified bacterial host cell of the present invention, comprising (a) introducing a nucleic acid encoding the NRPS operatively linked to a promoter capable of expressing the NRPS in the host cell into the host cell.

In some embodiments, the NRPS is heterologous to the host cell. In some embodiments, the NRPS is a bacterial NRPS. In some embodiments, the NRPS is a *Streptomyces lavendulae* NRPS (BpsA). In some embodiments, the NRPS comprises an amino acid sequence that is at least 70%, 80%, 90%, 95%, or 99% identical to the amino acid sequence of SEQ ID NO:1, wherein the NRPS comprises the enzymatic activity to convert glutamine to indigoidine.

The present invention provides for a method for a genetically modified bacterial host cell producing indigoidine, comprising (a) providing a genetically modified bacterial host cell of the present invention, (b) culturing or growing the host cell in a suitable culture or medium such that indigoidine is produced, and (c) optionally extracting or separating the indigoidine from the rest of the culture or medium, and/or host cell.

The present invention provides for a method for constructing a genetically modified bacterial host cell of the present invention, comprising (a) introducing a nucleic acid encoding the NRPS operatively linked to a promoter capable of expressing the NRPS in the host cell into the host cell.

Indigoidine is a redox active blue pigment that has documented use as a dye. It can also serve as a respiration signal in cultivation optimizations and has the chemical structure of a molecule that can be used in development of biomaterials (e.g. polymers). The pigment may be used to report the redox and respiratory state of a large culture that may be critical for production performance. In some embodiments, the invention comprises the use of a heterologous codon-optimized version of an NRPS in a bacterial host cell.

BRIEF DESCRIPTION OF THE DRAWINGS

The foregoing aspects and others will be readily appreciated by the skilled artisan from the following description of illustrative embodiments when read in conjunction with the accompanying drawings.

FIG. 2A. RNAseq analysis of plasmid-borne gRNA array in *P. putida*.

DETAILED DESCRIPTION OF THE INVENTION

Figure 1A:
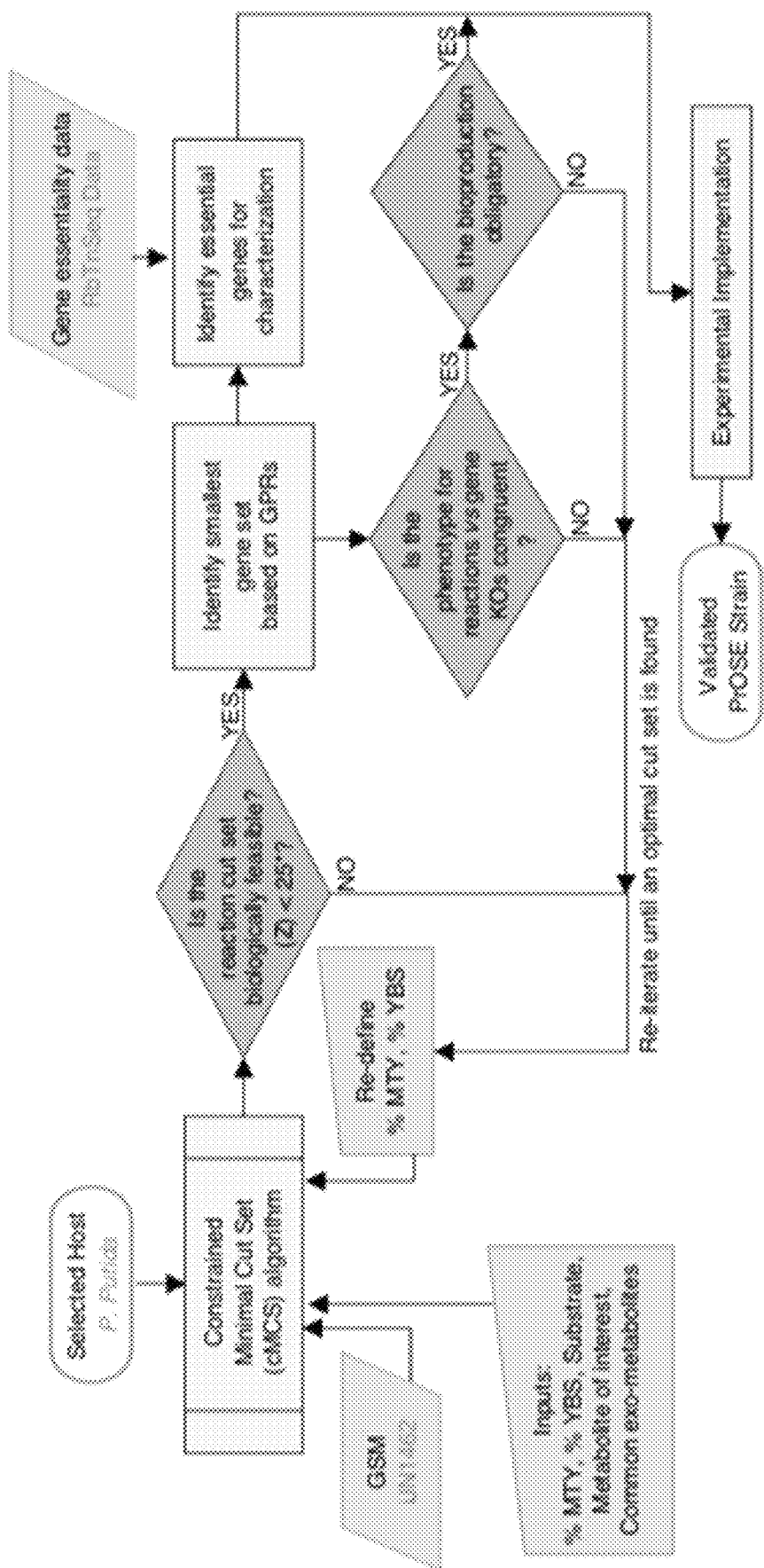
FIG. 1A. Product Obligatory Strain Engineering (PrOSE) workflow diagram. PrOSE can potentially be extended to any carbon source, host and/or metabolite. Inputs specific to this specific host/final product PrOSE work is marked in green font.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "cell" includes a single cell as well as a plurality of cells; and the like.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "cell" includes a single cell as well as a plurality of cells; and the like.

The term "about" refers to a value including 10% more than the stated value and 10% less than the stated value.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The terms "host cell" is used herein to refer to a living biological cell that can be transformed via insertion of an expression vector.

The term "heterologous" as used herein refers to a material, or nucleotide or amino acid sequence, that is found in or is linked to another material, or nucleotide or amino acid sequence, wherein the materials, or nucleotide or amino acid sequences, are foreign to each other (i.e., not found or linked together in nature).

The terms "expression vector" or "vector" refer to a compound and/or composition that transduces, transforms, or infects a host cell, thereby causing the cell to express nucleic acids and/or proteins other than those native to the cell, or in a manner not native to the cell. An "expression vector" contains a sequence of nucleic acids (ordinarily RNA or DNA) to be expressed by the host cell. Optionally, the expression vector also comprises materials to aid in achieving entry of the nucleic acid into the host cell, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host cell and replicated therein. Particular expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The terms "polynucleotide" and "nucleic acid" are used interchangeably and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); positive backbones; non-ionic backbones, and non-ribose backbones. Thus, nucleic acids or polynucleotides may also include modified nucleotides that permit correct read-through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

The term "promoter," as used herein, refers to a polynucleotide sequence capable of driving transcription of a DNA sequence in a cell. Thus, promoters used in the polynucleotide constructs of the invention include cis- and trans-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. Promoters are located 5' to the transcribed gene, and as used herein, include the sequence 5' from the translation start codon (i.e., including the 5' untranslated region of the mRNA, typically comprising 100-200 bp). Most often the core promoter sequences lie within 1-2 kb of the translation start site, more often within 1 kbp and often within 500 bp of the translation start site. By convention, the promoter sequence is usually provided as the sequence on the coding strand of the gene it controls. In the context of this application, a promoter is typically referred to by the name of the gene for which it naturally regulates expression. A promoter used in an expression construct of the invention is referred to by the name of the gene. Reference to a promoter by name includes a wildtype, native promoter as well as variants of the promoter that retain the ability to induce expression. Reference to a promoter by name is not restricted to a particular species, but also encompasses a promoter from a corresponding gene in other species.

A polynucleotide is "heterologous" to a host cell or a second polynucleotide sequence if it originates from a foreign species, or, if from the same species, is modified from its original form. For example, when a polynucleotide encoding a polypeptide sequence is said to be operably linked to a heterologous promoter, it means that the polynucleotide coding sequence encoding the polypeptide is derived from one species whereas the promoter sequence is derived from another, different species; or, if both are derived from the same species, the coding sequence is not naturally associated with the promoter (e.g., is a genetically engineered coding sequence, e.g., from a different gene in the same species, or an allele from a different ecotype or variety).

The term "operatively linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a DNA or RNA sequence if it stimulates or modulates the transcription of the DNA or RNA sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The present invention includes the following: using *Pseudomonas putida* KT2440 and a minimal cut set modeling to predict genes that when deleted would to lock growth to indigoidine (or glutamine) production. Very strongest conditions are used to strongly lock the growth with production. The resulting model predicted 16 genes would redirect metabolic flux to favor the desired precursor, indigoidine. The genes that needed to be edited included both non-essential and essential genes. Since essential genes cannot be deleted, an inducible, endonuclease-dead CRISPR based strategy is used to simultaneously target genes for repression. This present invention includes the resulting engineered strain and the sequential approach taken to maximize the production to theoretical max, fast rates and also low variation. This present invention includes the following embodiments:

1. Use of a genomically integrated bioproduction pathway in *P. putida* KT2440.
2. Optimization of cultivation conditions to maximize production.
3. Use of a metabolic modeling approach to predict a set of genes that were hitherto never implicated in the production and the use of an inducible, endonuclease-dead (dCpf1) CRISPR approach for the first time to edit all 16 genes, or any other set of genes, predicted.

In a particular embodiment, the genetically modified bacterial host cell is capable of the production of indigoidine using 1% (56 mM) glucose of up to about 7.2 g/L, which is about 98% of the theoretical max yield from glucose (n=6), from reaction stoichiometry and redox balance (at 48 hours, CV=6.9%, n=6). In a 2 L fed-batch production campaign, the growth coupled strain produces about 44.4 g/L indigoidine from 60 g/L glucose, which is 74% theoretical max yield from this carbon source.

This approach has allows for a novel systematic approach to reach near the theoretical yield using a set of predicted steps. This is a highest known yield of this compound from glucose as a sole carbon source.

In some embodiments, bacterial host cell is *P. putida* KT2440 (Biorxiv DOI number: 10.1101/139121), which is publicly available.

The basic concept of constrained minimal cut set (cMCS) is published and can be found in the webpage for "doi.org/10.1016/j.ymben.2010.12.004". Software code for cMCS analysis, all calculations are done using API functions of CellNetAnalyzer (webpage for: doi.org/10.1186/1752-0509-1-2) on MATLAB 2017b platform using CPLEX 12.8 as the MILP solver. An example script to calculate cMCS for growth-coupled product synthesis available at: the webpage for: mpi-magde-burg.mpg.de/projects/cna/etcdownloads.html, which is modified for *P. putida* KT2440 and substrates other than glucose (xylose, p-coumarate and galactose).

During strain engineering for bioproduction, maximizing the metabolic output remains unsystematic. Robust production often relies on good growth though production and growth are often at odds with each other, leading to phenotypic drift and eventually unstable/unreliable production. To disrupt this paradigm, an approach is developed to engineer a bacterial production strain where growth and the production of the desired final product are strongly locked. Specifically, in *Pseudomonas putida* KT2440 a minimal cut set modeling is used to predict genes that when deleted would to lock growth to indigoidine (or glutamate) production. Very strongest conditions are used to strongly lock the growth with production. The resulting model predicts 16 genes would redirect metabolic flux to favor the desired precursor, indigoidine. The genes that needed to be edited included both non-essential and essential genes. Since essential genes cannot be deleted, an inducible, endonuclease-dead CRISPR based strategy is used to simultaneously target genes for repression.

By taking a stringent modeling approach one predicts gene edits that would strongly lock growth with production. In other words, if there is no production there will be no growth (rather than the reverse). This forces metabolic flux to be maintained towards the pathway of choice. In order to develop the resulting strain—reduction to practice—that could demonstrate this phenotype, first one has to generate a baseline strain with low variability and cultivation/production parameters. In some embodiments, the method comprises one or more of the following:

(1) Integrating the gene pathway leads to more reproducible final titers of indigoidine compared to a plasmid-borne pathway. In some embodiments, expression of the heterologous pathway in *P. putida* using pTE302 (integrated indigoidine production) vs. pTE252: (plasmid-borne). The genomically-integrated heterologous gene pathway results in <10% variation (CV of this sample is 8.98%, n=12). With a plasmid borne system, coefficient of variation is 57.5%, n=12

(2) The optimal starting concentration of glucose for the production of indigoidine is 1% (56 mM) glucose and between 30 mM-100 mM $(NH_4)_2SO_4$ in M9 minimal salt media. This is based on optimization of media conditions that leverages our expert knowledge and relates to a relationship between starting glucose concentration and indigoidine titer.

(3) A growth locked strategy for the production of indigoidine results in metabolic flux to reach 98% of the calculated maximum theoretical yield. Per our minimal cut set modeling, the Growth Locked Strategy to Maximize Intracellular Glutamine for the Production of Indigoidine identify 16 genes to be deleted. These 16 genes are involved in 14 reactions that belonged to the only minimal cut set predicted for a minimum product yield of 80% and minimum biomass yield of 10%. The indigoidine biosynthesis reactions are added to the *P. putida* KT2440 model and checked for growth locked production of indigoidine. These genes targets have never been predicted for such an application before and are a novel claim. These genes include essential genes as are: PP_1444, PP_2082, PP_0654, PP_1251, PP_5085, PP_2168, PP_5186, PP_0864, PP_4947, PP_5003, PP_0434, PP_4735, PP_2925, PP_5005, PP_0100, and PP_0751.

To address editing a large number of genes including essential genes a dCpf1 endonuclease variant was developed for a dCpf1/CRISPRi based gene targeting approach in *P. putida* KT2440. pTE314 is a dCpf1 plasmid for growth coupled strategy to maximize glutamine production. pTE327 is a revised dCpf1 plasmid, growth coupled for glutamine, no essential genes targeted. Using a multiplex CRISPR interference strategy all 16 genes are targeted for gene silencing.

Result: As predicted by the model—the engineered strain with 16 deleted genes and a genomically integrated production pathway had massive improvement of indigoidine production rate, yield, titer, and reproducibility). The production of indigoidine using 1% (56 mM) glucose was 7.2 g/L, which is 98% of the theoretical max yield from glucose (n=6), from reaction stoichiometry and redox balance (at 48 hours, CV=6.9%, n=6). In a 2 L fed-batch production campaign, the growth coupled strain produced 44.4 g/L indigoidine from 60 g/L glucose, which is 74% theoretical max yield from this carbon source. This is the first reduction to practice of a theoretical growth coupled strategy targeting more than 3 genes for repression. Directly, this provides a highly reliable and high efficiency platform for the production of Indigoidine in a bacterial host *P. putida* from glucose. Indigoidine has direct uses in dye and pigment industry.

The approach for the development of this host provides a general route for increasing yield and reducing variation in heterologous product formation in *P. putida* and other hosts.

Directly, for the production of Indigoidine it provides a platform that uses renewable carbon sources and reaches close to theoretical max. It is also a highly stable system due to its growth being genetically coupled to production of Indigoidine. Unlike most other systems—in this engineered strain the exact levels of glucose to be used and the amount of product formed can be predicted and will result superior process downstream product development.

This approach for host development provides a rationale for synchronizing the host metabolism with the heterologous pathway. It results in a superior production system for increasing yield and reduces variation in heterologous product formation. Predicting the timeframe and productivity of such a host is greater than hosts that have not been synced in this manner. Engineering the host in this manner may also overcome natural drifts that occur due to mutations, because in this strain production is required for growth.

As alternate CRISPR systems are characterized, multiple CRISPR proteins can be expressed in the same cell, each under the control of a different carbon-responsive promoter. Strong growth coupling strategies can be implemented for two different carbon sources, such as glucose and xylose. The expression of a xylose specific CRISPR (i.e., Cas9) would also inactivate the other CRISPR system (in this case, Cpf1), ensuring that only one growth coupling strategy is used even in the presence of multiple carbon sources.

The present invention provides for a genetically modified bacterial host cell capable of producing indigoidine, wherein the host cell comprises a non-ribosomal peptide synthetase (NRPS) that converts glutamine to indigoidine.

In some embodiments, the NRPS is heterologous to the host cell. In some embodiments, the NRPS is a bacterial NRPS. In some embodiments, the NRPS is a *Streptomyces lavendulae* NRPS (BpsA). In some embodiments, the NRPS comprises an amino acid sequence that is at least 70%, 80%, 90%, 95%, or 99% identical to the amino acid sequence of SEQ ID NO:1, wherein the NRPS comprises the enzymatic activity to convert glutamine to indigoidine.

In some embodiments, the NRPS comprises a conserved domain, such as the amino acid sequence APRTETEKEI AEVWAKSLRR ESVSVQDDFF ESGGNSLIAV GLIRELNSRL GVSLPLQSVL ESPTVEKLSR RLEREV (SEQ ID NO:2), at the position corresponding to 937 to 1012 of SEQ ID NO:1.

In some embodiments, the NRPS comprises a coiled coil structure, such as the amino acid sequence SRRLEREV (SEQ ID NO:3), or SRRLEREVAQESSRLVRLHAE (SEQ ID NO:4), at the position corresponding to 1005 to 1012, or 1005 to 1025, of SEQ ID NO:1, respectively.

In some embodiments, the serine at position 972 is a modified serine, such as O-(pantetheine 4'-phosphoryl)serine.

The amino acid sequence of *Streptomyces lavendulae* BpsA is as follows:

```
                                                 (SEQ ID NO: 1)
         10         20         30         40
MTLQETSVLE PTLRGTTTLP DLLAKRVAEH PEATAVAYRD 50         60         70         80
EKLTYRELAS RSSALAEYLR HLGVSTDDCV GLFVEPSIDL 90        100        110        120
MVGAWGILSA GAAYLPLSPE YPEDRLRYMI ENSQAKIILA 130        140        150        160
QQRLVTRLRE LAPQDVRVVT LRESEAFVLP EGQVAPAIEG 170        180        190        200
ARPDSLAYVI YTSGSTGKPK GVMIEHHSIV SQLGWLRETY 210        220        230        240
GIDRSKTILQ KTPMSFDAAQ WEILSPANGA TVVMGAPGVY 250        260        270        280
ADPEGLIETI VKYGVTTLQC VPTLLQGLLD TEKFPECTSL 290        300        310        320
QQIFSGGEAL SRLLAIQTTQ EMPGRALINV YGPTECTINS 330        340        350        360
SSYAVDPAEL GEAPQSISIG APVADTEYHI LGKEDLKPVG 370        380        390        400
VGEIGELYIG GGQLARGYLH RPDLTAERFL EIEVTEGAGP 410        420        430        440
VRLYKTGDLG QWNPDGTVQF AGRADNQVKL RGYRVELDEI 450        460        470        480
SLAIENHDWV RNAAVIVKND GRTGFQNLIA CVELSEKEAA 490        500        510        520
LMDQGNHGSH HASKKENLQY KAQLSNPGLR DDADLAARVA 530        540        550        560
YDLPGAEPTP EQRSRVFARK TYRFYEGGAV TEADLLALLG 570        580        590        600
GQVPAAYSRK AADLAPAELG QILRWFGQYL SEERLLPKYG 610        620        630        640
YASPGALYAT QLYFFLEGVG GLQPGYYYYQ PQRHQLVLIS 650        660        670        680
EKAATGRPTA HIHFIGNRGG IEPVYKNNIQ EVLEIETGHI 690        700        710        720
VGLFEQVLPA YGLDIRDLAY EPAVRDLLDV PEEDFYLGTF 730        740        750        760
ELVPHTGRRE DHAEVYVQTH GSKVANLPEG QYRYADGTLT 770        780        790        800
RFSDDIVLKX QVIAINQSVY QAASFGISVI SRAPEEWMHY 810        820        830        840
VTLGKYLOHL MMNGLGLGFM SSGYSSKTGN PLPASRRIDS 850        860        870        880
VLQANGVESG PSYFFVGGRV SDEQLGHEGM REDSVHMRGP 890        900        910        920
AELIRDDLVS FLPDYMIPNR VVVFERLPLS ANGKIDAKAL 930        940        950        960
AASDQVNAEL VERPFVAPRT ETEKEIAEVW AKSLRRESVS 970        980        990       1000
VQDDFFESGG NELIAVGLIR ELNSRLGVSL PLQSVLESPT 1010       1020       1030       1040
VFKLSRRLER EVAQESSRLV RLHAETGKDR PVLCWPGLGG 1050       1060       1070       1080
YPMNLRTLAG EIGLGRSFYG IQAHGINEGE APYATITEMA 1090       1100       1110       1120
KADIEAIKEL QPKGPYTLWG YSFGARVAFE TAYQLEQAGE 1130       1140       1150       1160
KVDNLFLIAP GSPTVRAENG KVYGREASFA NRAYTTILFS 1170       1180       1190       1200
VYTGTISGPD LEKCLESATD EESFAGFISE LKGIDVDLAK 1210       1220       1230       1240
RIISVVGQTY EFEYSFRELA ERTLAAPVTI FKARGDDYSF 1250       1260       1270       1280
IENSNGYSAE PPTVIDLDAD HYSLLRTPDI GELVKHIRYL LGE
```

In some embodiments, the host cell comprises a nucleic acid encoding the NRPS operatively linked to a promoter capable of expressing the NRPS in the host cell. In some embodiments, the encoding of the NRPS to the nucleic acid is codon optimized to the bacterial host cell. In some embodiments, the nucleic acid is vector or replicon that can stably reside in the host cell. In some embodiments, the nucleic acid is stably integrated into one or more chromosomes of the host cell.

The present invention provides for a method for a genetically modified bacterial host cell producing indigoidine, comprising (a) providing a genetically modified bacterial host cell of the present invention, (b) culturing or growing the host cell in a suitable culture or medium such that indigoidine is produced, and (c) optionally extracting or separating the indigoidine from the rest of the culture or medium, and/or host cell.

In some embodiments, the providing step (a) comprises introducing a nucleic acid encoding the NRPS operatively linked to a promoter capable of expressing the NRPS in the host cell into the host cell.

In some embodiments, the culturing or growing step (b) comprises the host cell growing by respiratory cell growth. In some embodiments, the culturing or growing step (b) takes place in a batch process or a fed-batch process, such as a high-gravity fed-batch process. In some embodiments, the culture or medium comprises hydrolysates derived or obtained from a biomass, such as a lignocellulosic biomass. In some embodiments, the culture or medium comprises one or more carbon sources, such as a sugar, such as glucose or galactose, or glycerol, or a mixture thereof. In some embodiments, the carbon source is fermentable. In some embodiments, the carbon source is non-fermentable.

The present invention provides for a method for constructing a genetically modified bacterial host cell of the present invention, comprising (a) introducing a nucleic acid encoding the NRPS operatively linked to a promoter capable of expressing the NRPS in the host cell into the host cell.

One can modify the expression of a gene encoding any of the enzymes taught herein by a variety of methods in accordance with the methods of the invention. Those skilled in the art would recognize that increasing gene copy number, ribosome binding site strength, promoter strength, and various transcriptional regulators can be employed to alter an enzyme expression level.

References cited herein:
1. Casini, A. et al. A pressure test to make 10 molecules in 90 days: external evaluation of methods to engineer biology. *J. Am. Chem. Soc.* 140, 4302-4316 (2018).
2. Wehrs, M. et al. Engineering Robust Production Microbes for Large-Scale Cultivation. *Trends Microbiol.* 27, 524-537 (2019).
3. Baral, N. R. et al. Techno-economic analysis and life-cycle greenhouse gas mitigation cost of five routes to bio-jet fuel blendstocks. *Energy Environ. Sci.* 12, 807-824 (2019).
4. Lievense, J. Scaling up Industrial Biotechnology. in (Life Science & Technology Programme of Delft University of Technology and Leiden University, 2016). at <webpage for: genomatica.com/wp-content/uploads/2017/01/20160510-7th-Life-Sci-Symp-Lievense.pdf>
5. Delvigne, F., Takors, R., Mudde, R., van Gulik, W. & Noorman, H. Bioprocess scale-up/down as integrative enabling technology: from fluid mechanics to systems biology and beyond. *Microb. Biotechnol.* 10, 1267-1274 (2017).
6. Crater, J. S. & Lievense, J. C. Scale-up of industrial microbial processes. *FEMS Microbiol. Lett.* 365, (2018).
7. Zahniser, S. et al. *The Growing Corn Economies of Mexico and the United States*. (US Department of Agriculture, Economic Research Service, 2019). at <webpage for: ers.usda.gov/webdocs/publications/93542/ocs-19f-02.pdf?v=9932.1>
8. OECD & Food and Agriculture Organization of the United Nations. *OECD-FAO Agricultural Outlook 2018-2027*. (OECD, 2018). doi:10.1787/agr_outlook-2018-en
9. Newsome, A. G., Culver, C. A. & van Breemen, R. B. Nature's palette: the search for natural blue colorants. *J. Agric. Food Chem.* 62, 6498-6511 (2014).
10. Bloudoff, K. & Schmeing, T. M. Structural and functional aspects of the nonribosomal peptide synthetase condensation domain superfamily: discovery, dissection and diversity. *Biochim. Biophys. Acta Proteins Proteom.* 1865, 1587-1604 (2017).
11. Nogales, J. et al. High-quality genome-scale metabolic modeling of *Pseudomonas putida* highlights its broad metabolic capabilities. *Environ. Microbiol.* (2019). doi: 10.1111/1462-2920.14843
12. Hädicke, O. & Klamt, S. Computing complex metabolic intervention strategies using constrained minimal cut sets. *Metab. Eng.* 13, 204-213 (2011).
13. von Kamp, A. & Klamt, S. Growth-coupled overproduction is feasible for almost all metabolites in five major production organisms. *Nat. Commun.* 8, 15956 (2017).
14. Thompson, M. G. et al. Massively Parallel Fitness Profiling Reveals Multiple Novel Enzymes in *Pseudomonas putida* Lysine Metabolism. *MBio* 10, (2019).
15. Price, M. N. et al. Mutant phenotypes for thousands of bacterial genes of unknown function. *Nature* 557, 503-509 (2018).
16. Ajikumar, P. K. et al. Isoprenoid pathway optimization for Taxol precursor overproduction in *Escherichia coli*. *Science* 330, 70-74 (2010).
17. Dunlop, M. J. et al. Engineering microbial biofuel tolerance and export using efflux pumps. *Mol. Syst. Biol.* 7, 487 (2011).
18. Weickert, M. J. & Adhya, S. The galactose regulon of *Escherichia coli*. *Mol. Microbiol.* 10, 245-251 (1993).
19. Holden, H. M., Rayment, I. & Thoden, J. B. Structure and function of enzymes of the Leloir pathway for galactose metabolism. *J. Biol. Chem.* 278, 43885-43888 (2003).
20. Takahashi, H. et al. Cloning and characterization of a *Streptomyces* single module type non-ribosomal peptide synthetase catalyzing a blue pigment synthesis. *J. Biol. Chem.* 282, 9073-9081 (2007).
21. Verstrepen, K. J., Jansen, A., Lewitter, F. & Fink, G. R. Intragenic tandem repeats generate functional variability. *Nat. Genet.* 37, 986-990 (2005).
22. Bzymek, M. & Lovett, S. T. Instability of repetitive DNA sequences: the role of replication in multiple mechanisms. *Proc Natl Acad Sci USA* 98, 8319-8325 (2001).
23. Reis, A. C. et al. Simultaneous repression of multiple bacterial genes using nonrepetitive extra-long sgRNA arrays. *Nat. Biotechnol.* 37, 1294-1301 (2019).
24. Barrangou, R. et al. CRISPR provides acquired resistance against viruses in prokaryotes. *Science* 315, 1709-1712 (2007).
25. Straight, A. F., Belmont, A. S., Robinett, C. C. & Murray, A. W. GFP tagging of budding yeast chromosomes reveals that protein-protein interactions can mediate sister chromatid cohesion. *Curr. Biol.* 6, 1599-1608 (1996).
26. Zetsche, B. et al. Cpf1 is a single RNA-guided endonuclease of a class 2 CRISPR-Cas system. *Cell* 163, 759-771 (2015).
27. Mehrer, C. R. et al. Growth-coupled bioconversion of levulinic acid to butanone. *Metab. Eng.* 55, 92-101 (2019).
28. Lo, T.-M., Chng, S. H., Teo, W. S., Cho, H.-S. & Chang, M. W. A Two-Layer Gene Circuit for Decoupling Cell Growth from Metabolite Production. *Cell Syst.* 3, 133-143 (2016).
29. Alter, T. B. & Ebert, B. E. Determination of growth-coupling strategies and their underlying principles. *BMC Bioinformatics* 20, 447 (2019).
30. Klamt, S. & Mahadevan, R. On the feasibility of growth-coupled product synthesis in microbial strains. *Metab. Eng.* 30, 166-178 (2015).
31. Yim, H. et al. Metabolic engineering of *Escherichia coli* for direct production of 1,4-butanediol. *Nat. Chem. Biol.* 7, 445-452 (2011).

32. Shen, C. R. et al. Driving forces enable high-titer anaerobic 1-butanol synthesis in *Escherichia coli*. *Appl. Environ. Microbiol.* 77, 2905-2915 (2011).
33. Lan, E. I. & Liao, J. C. ATP drives direct photosynthetic production of 1-butanol in cyanobacteria. *Proc Natl Acad Sci USA* 109, 6018-6023 (2012).
34. Wang, J. et al. Developing a pyruvate-driven metabolic scenario for growth-coupled microbial production. *Metab. Eng.* 55, 191-200 (2019).
35. Shabestary, K. & Hudson, E. P. Computational metabolic engineering strategies for growth-coupled biofuel production by Synechocystis. *Metab. Eng. Commun.* 3, 216-226 (2016).
36. von Kamp, A. & Klamt, S. Enumeration of smallest intervention strategies in genome-scale metabolic networks. *PLoS Comput. Biol.* 10, e1003378 (2014).
37. Xu, F., Gage, D. & Zhan, J. Efficient production of indigoidine in *Escherichia coli*. *J. Ind. Microbiol. Biotechnol.* 42, 1149-1155 (2015).
38. Wehrs, M. et al. Production efficiency of the bacterial non-ribosomal peptide indigoidine relies on the respiratory metabolic state in *S. cerevisiae*. *Microb. Cell Fact.* 17, 193 (2018).
39. Wehrs, M. et al. Sustainable bioproduction of the blue pigment indigoidine: Expanding the range of heterologous products in *R. toruloides* to include non-ribosomal peptides. *Green Chem.* (2019). doi:10.1039/C9GC00920E
40. Mukhopadhyay, A. Tolerance engineering in bacteria for the production of advanced biofuels and chemicals. *Trends Microbiol.* 23, 498-508 (2015).
41. George, K. W., Alonso-Gutierrez, J., Keasling, J. D. & Lee, T. S. Isoprenoid drugs, biofuels, and chemicals—artemisinin, farnesene, and beyond. *Adv. Biochem. Eng. Biotechnol.* 148, 355-389 (2015).
42. Withers, S. T., Gottlieb, S. S., Lieu, B., Newman, J. D. & Keasling, J. D. Identification of isopentenol biosynthetic genes from *Bacillus subtilis* by a screening method based on isoprenoid precursor toxicity. *Appl. Environ. Microbiol.* 73, 6277-6283 (2007).
43. Klamt, S., Saez-Rodriguez, J. & Gilles, E. D. Structural and functional analysis of cellular networks with CellNetAnalyzer. *BMC Syst. Biol.* 1, 2 (2007).
44. Heirendt, L. et al. Creation and analysis of biochemical constraint-based models using the COBRA Toolbox v.3.0. *Nat. Protoc.* 14, 639-702 (2019).
45. Salvachúa, D., Karp, E. M., Nimlos, C. T., Vardon, D. R. & Beckham, G. T. Towards lignin consolidated bioprocessing: simultaneous lignin depolymerization and product generation by bacteria. *Green Chem.* 17, 4951-4967 (2015).
46. Rio, D. C., Ares, M., Hannon, G. J. & Nilsen, T. W. Purification of RNA using TRIzol (TRI reagent). *Cold Spring Harb. Protoc.* 2010, pdb.prot5439 (2010).
47. Eng, T. et al. Restoration of biofuel production levels and increased tolerance under ionic liquid stress is enabled by a mutation in the essential *Escherichia coli* gene cydC. *Microb. Cell Fact.* 17, 159 (2018).

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

EXAMPLE 1

Genome-Scale Metabolic Rewiring to Achieve Predictable Titers Rates and Yield of Non-Native Products at Scale Achieving high titer rates and yields (TRY) remains a bottleneck for the production of heterologous products in microbial systems, requiring elaborate engineering and many iterations. Reliably scaling engineered strains also remains risky and is rarely addressed in the first designs of the engineered strains. Both high TRY and scale are challenging due to the inherent trade-off between cellular use of carbon towards growth and target metabolite production. It is hypothesized that being able to strongly couple product formation with growth may enable both high TRY and reliability across scale. In this Example, elementary mode analysis is used to predict metabolic reactions that could be targeted to lock the production of indigoidine, a sustainable pigment, with the growth of the chosen host, *P. putida* KT2440. The set of 16 predicted reactions is then filtered using -omics data and the final 14 gene knockdowns is implemented using a CRISPRi method optimized for *P. putida*. It is demonstrated that product obligatory regime could be implemented, and the 14-gene engineered *P. putida* strain could achieve high TRY. Further, due to dependence on product formation, the strain maintains its high TRY phenotype across scale. This approach is called PrOSE: product obligatory strain engineering. The *P. putida* PrOSE strain, in one design cycle, is able to demonstrate close to 50% maximum theoretical yield (0.33 g/g of glucose consumed), reaching 25.6 g/L indigoidine from glucose and shifted production from stationary to exponential phase. These desirable phenotypes are maintained from batch to fed batch, and from lab to 250 ml AMBR to 2 L bioreactor.

In this Example, it is explored if it is possible to rewire the metabolism of the host strain such that production of a final product or a key intermediate becomes obligatory for its growth, thereby maximizing and maintaining productivity at scale.

Native microbial processes that take such an obligatory production route include production of ethanol and organic acids during fermentation. Production of these metabolites are required during fermentative growth, and correspondingly these compounds represent the most prominent examples of successful high-volume bioproduction[7,8]. It is hypothesized that obligatory production to growth is implementable for a heterologous product, and that such coupling could provide the desirable production characteristics. These key characteristics are the ability to reach high TRY and the ability to maintain production parameters across different growth modes and scales. A general approach for success in these two aspects represents a new paradigm for strain engineering that can directly achieve a production system with genuine industrial relevance.

The availability of comprehensive metabolic models and genome editing tools in a wide variety of microbes suitable for industrial use provides the foundation for PrOSE. The production of indigoidine, a bipyridyl compound derived from glutamine, is used as the target heterologous product.

Both as a sustainable replacement for blue pigments[9] in a wide array of applications as well as a model non-ribosomal peptide[10], this compound provides a valuable target to explore. *Pseudomonas putida* KT2440 is used as the production host, leveraging the availability of the iJN1462 genome scale model for *P. putida* KT2440[11]. Elementary mode analysis (EMA)[12] is adapted to determine the constrained minimal cut set (cMCS) required to minimize metabolic flux towards undesired products and link indigoidine formation to cell viability[13]. These analyses combined with publicly available omics data[14,15] provide the set of gene loci that represented the reactions necessary for removal. The corresponding set of gene loci are repressed using multiplex CRISPR interference (CRISPRi) that is optimized for use in *P. putida* KT2440.

Such an implementation results in a highly edited strain that, in a single iteration of strain engineering, achieves close to 50% max theoretical yield of indigoidine in *P. putida* KT2440 and TRY characteristics that maintain fidelity from laboratory to industrially relevant scales. The specific aspects of our systems, the PrOSE approach, its implementation, and other beneficial characteristics demonstrated by the PrOSE strain are described in this study.

RESULTS

Genome Scale Evaluation of *P. putida* for Production-Obligatory Growth

To develop the PrOSE approach (FIG. 1A), it is first explored how many of the represented metabolites in *P. putida* iJN1462[11] model can be made obligatory for growth. For this the cMCS algorithm[13] is used to identify minimal sets of reactions, the elimination of which would cause production of a given metabolite to become essential for growth. Aerobic conditions with glucose as the sole carbon source are used to model growth parameters. The theoretical yield is $Y_{Product/Substrate}$, hereafter referred to as $Y_{P/S}$. Gene knockdown sets are searched to satisfy three potential constraints in which $Y_{P/S}$ is at minimum, 10%, 50%, or 80% of the maximum theoretical yield (MTY) for all producible metabolites in the model. This analysis is completed for all 2145 metabolites in the genome scale model, which indicates that 979 organic metabolites could be potentially growth coupled using under these growth conditions. In the first pass, 95.7% of all metabolites had the potential to be obligatory for growth, with a minimum threshold of 10% MTY (Table 2); this is consistent for similar calculation for other hosts[13]. When the threshold for minimum production is set to 50% MTY, 950 metabolites could be obligatory for growth; for an 80% threshold MTY, only 343 metabolites could be obligatory for growth, representing only 35% of the total producible metabolites. Thus setting the higher the threshold for minimum product yield results in fewer metabolites that can be used to implement a production obligatory regime.

TABLE 2

|  | Organism | |
|---|---|---|
|  | *P. putida* KT2440 | *E. coli* MG1655[1] |
| GSM Model | iJN1462 | iJO1366 |
| Internal metabolites | 2145[2] | 1805 |

TABLE 2-continued

|  | Organism | |
|---|---|---|
|  | *P. putida* KT2440 | *E. coli* MG1655[1] |
| Total Reactions | 2928 | 2582 |
| Repressible reactions | 2046 | 1414 |
| Irrepressible reactions | 882 | 1168 |
| Glucose uptake limit (mmol/gDW/h) | 6.3 | 15 |
| ATP maintenance (mmol/gDW/h) | 0.92 | 3.15 |
| Glucose-producible organic metabolites | 979 | 954 |
| Min yield (%) | 10 | 10 |
| Metabolites with feasibility of strong coupling | 937[3] | 954 |
| cMCS size |  |  |
| Min | 4[4] | 3 |
| Max | 48[5] | 50 |
| Mean | 18.6 | 17.4 |

[1]Results for *E. coli* were reported previously (von Kamp and Klamt 2017)
[2]892 unique metabolites
[3]95.7%
[4]Metabolites include 4-Hydroxy-L-threonine, Mannose-6-phosphate, Mannuronate
[5]Only one metabolite - Vaccenyl coenzyme A An in silico reaction for the heterologous product, indigoidine, is added to the genome scale metabolic model iJN1462[11]. This reaction represents the biosynthesis of indigoidine from glutamine and accounts for all cofactors needed. $Y_{P/S}$ for glutamine and indigoidine is calculated to be 1.141 mol/mol and 0.537 mol/mol respectively from glucose as the carbon source (Table 1). $Y_{P/S}$ for glutamine in *P. putida* is relatively high relative to other hosts screened (Table 3). As this method accounts for the other physiological processes competing for resources, a $Y_{P/S}$ derived from a genome scale model provides a more accurate assessment compared to simpler methods, as is commonly done in the field[16,17].

TABLE 1

Maximum theoretical yield of glutamine and indigoidine from three different substrates Glucose, Galactose and p-coumarate with respect to stoichiometry and redox balance in *P. putida*

|  | Yield (mol/mol) of Substrate | | |
|---|---|---|---|
| Metabolite | Glucose | Galactose | p-coumarate |
| Alpha-ketoglutarate | 1.32 | 1.366 | 1.651 |
| Glutamine | 1.141 | 1.181 | 1.408 |
| Indigoidine | 0.537 | 0.556 | 0.660 |

TABLE 3

Theoretical yields of glutamine and indigoidine across different industrial hosts.

| | Theoretical Maximum Yields From Glucose (mol/mol) | | | | |
|---|---|---|---|---|---|
| | P. putida | C. glutamicum | E. coli | R. toruloides | S. cerevisiae |
| | | | Genome-scale Model (GSM) | | |
| | iJN1462 (Nogales et al., 2019) | iCW773 (Zhang et al., 2017) | iML1515 (Monk et al., 2017) | iRhto1108C (Dinh et al., 2019) | iMM904 (Zomorrodi and Maranas, 2010) |
| Glutamine | 1.141 | 1 | 1.135 | 1.118 | 0.481 |
| Biomass | 0.098 | 0.092 | 0.088 | 0.075 | 0.029 |
| Indigoidine | 0.537 | 0.4* | 0.4 | 0.503* | 0.079* |
| | Constraints used for each of the GSMs to best represent cell phenotype | | | | |
| Glucose Uptake Rate (mmol/gDCW/hr) | 6.3 | 4.67 | 10 | 5 | 10 |
| ATP Maintenance demand (mmol/gDCW/hr) | 0.92 | 0 | 6.86 | 1.012 | 1 |

*No indigoidine formation if FMN is limiting. But the BpsA oxidation domain might be engineered such that FMN is not required for indigoidine production (Takahashi et al., 2007)

Figure 1B:
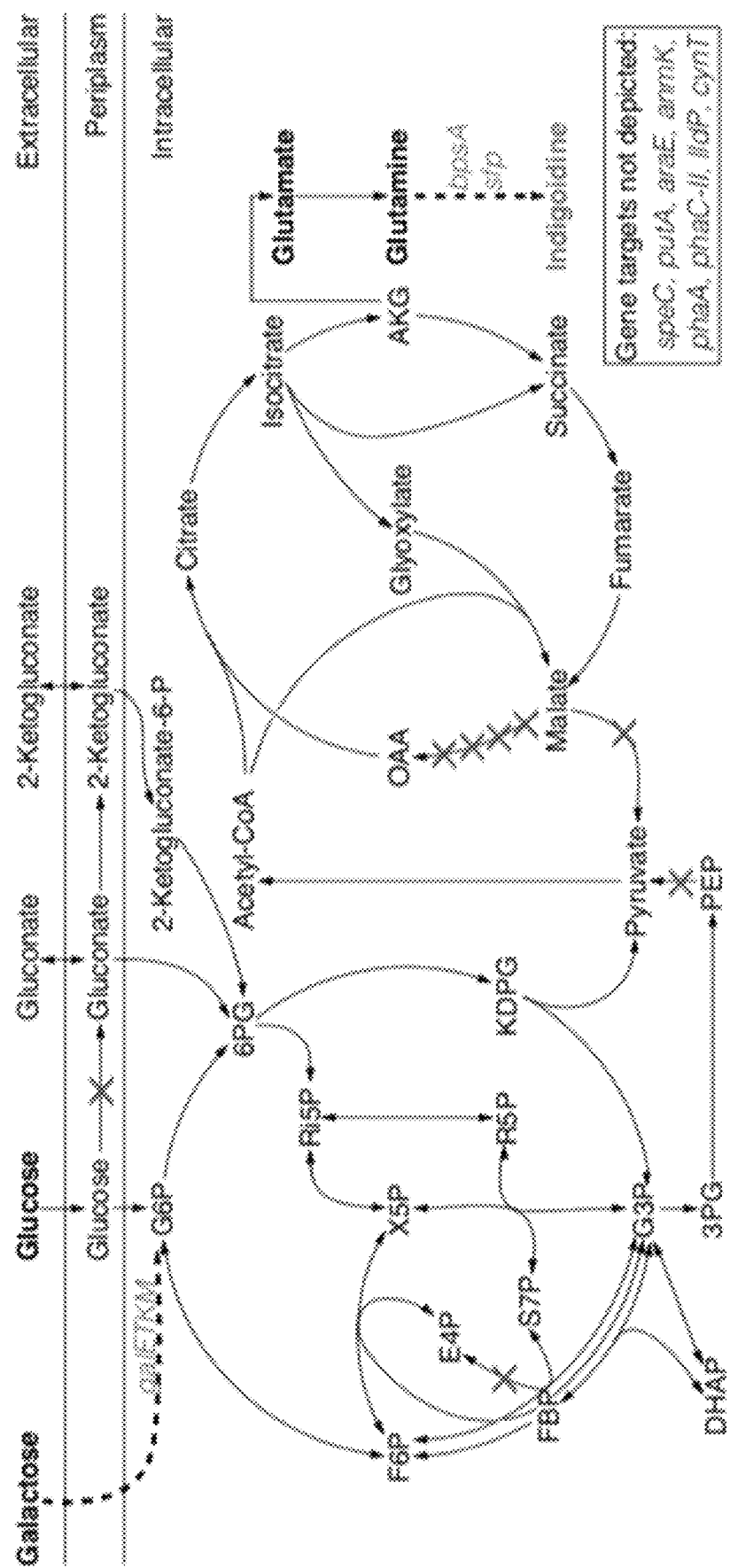
FIG. 1B: The central metabolism of *Pseudomonas putida* is engineered to produce indigoidine from either glucose or galactose. Heterologous genes are indicated in purple text. Indigoidine is derived from the TCA intermediate alpha-ketoglutarate (AKG) via two molecules of glutamine. The necessary metabolic reactions targeted for gene knockdown by dCpf1/CRISPRi are indicated with red X marks. Additional gene targets outside of *P. putida* central metabolism are indicated in the box on the bottom right. A total of 14 genes are targeted for CRISPR interference.

In order to predict reactions that would be required to improve indigoidine production, glutamine, its precursor, is used to conduct the analysis. The process for determining the list of required gene targets is diagrammed in FIG. 1A. The minimum $Y_{P/S}$ of glutamine is set at 10%, 50% and 80% to derive the reactions that would require knockout or knockdown for product obligatory growth. Potential target sets which required the removal of multi-functional gene products is eliminated, as it is sought to limit additional metabolic perturbations that could confound our analysis. Of the 1956 reactions in iJN1462 that are associated with genes, only 60% have a single gene associated with them. If a metabolic reaction is catalyzed by more than one gene (i.e., gene redundancy), both genes are included for inactivation. After implementing these filters, it is found that a threshold of 80% $Y_{P/S}$ could be achieved using the elimination of 14 cellular reactions. These 14 metabolic reactions when mapped to their corresponding genes and gene products represent 16 gene loci (FIG. 1B).

Next, using Flux Balance Analysis (FBA) and Flux Variability Analysis (FVA), it is confirmed the 16 gene cMCS strategy to be obligatory for glutamine production. Using the constructed cMCS platform, the parameters are set to explore potential product-obligatory strategies to enhance the production of indigoidine in P. putida when fed glucose as the sole carbon source. The focus is narrowed to a minimum glutamine production of 80% $Y_{P/S}$ and a minimum biomass yield of 0.01 gDW mmol$^{-1}$. This 16 gene set designed for glutamine is then extended to assess production obligatory growth for indigoidine. It is found that indigoidine production is obligatory with 90% theoretical yield of indigoidine (0.48 mol/mol glucose). This workflow allowed one to adapt the work from von Kamp and Klamt for non-native final products and predict specific genes rather than enzymatic reactions for knockdown.

To test the flexibility of this PrOSE strategy, the substrate utilization range is expanded to better match sugars found in emerging lignocellulosic hydrolysates. An analysis of suitable starting carbon sources indicated that cultivation with several amino acids or sugars (i.e. lysine, pCA) failed to produce glutamine (Table 4). P. putida can be engineered to express the minimal E. coli galETKM utilization pathway[18,19]. Interestingly, this gene targeting set results in production obligatory growth using galactose as a carbon source because both sugars share the same downstream catabolism (FIG. 1B).

TABLE 4

An analysis of suitable starting carbon sources indicated that cultivation with several amino acids or sugars (i.e. lysine, pCA) failed to produce glutamine.

| PrOSE works for following carbon sources | PrOSE fails to work for following carbon sources |
|---|---|
| Glycerol, Fructose, Mannose, Serine, Threonine, Galactose, Asparagine, Aspartate, Glycine, Homoserine, Xanthine | Lysine, Leucine, Succinate, Malate, Tryptophan, Tyrosine, Valine, Xylose, p-coumarate, Cysteine, Alphaketoglutarate |

Figure 3A:
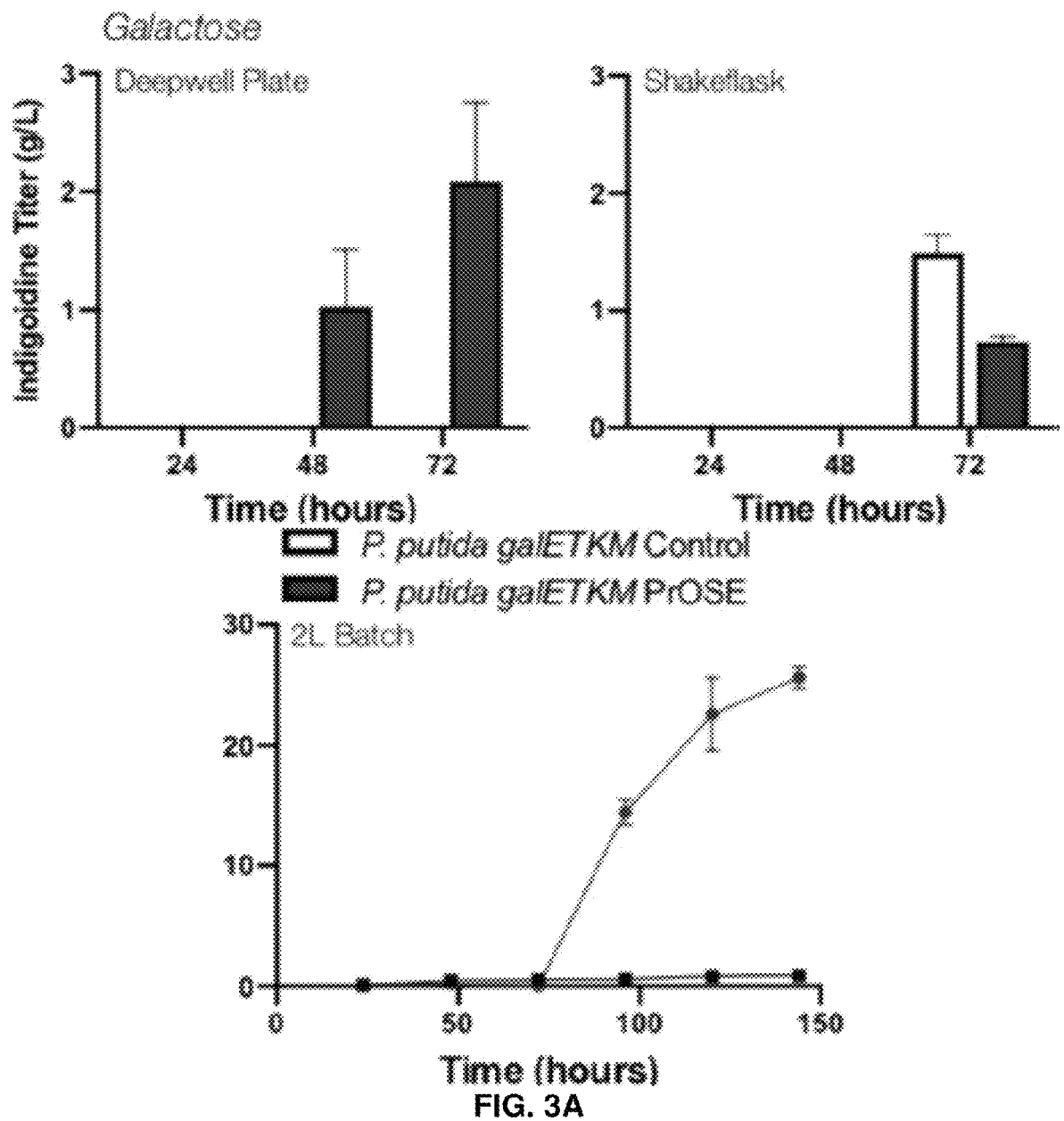
FIG. 3A. PrOSE Can Improve Titer Rate and Yield (TRY) Across Two Carbon Sources. Analysis of *P. putida* galETKM PrOSE strains and a control strain (*P. putida* galETKM, empty vector plasmid) for production of indigoidine using galactose as the sole carbon source in minimal salt media. The culture format assessed is indicated above each panel.
Figure 3B:
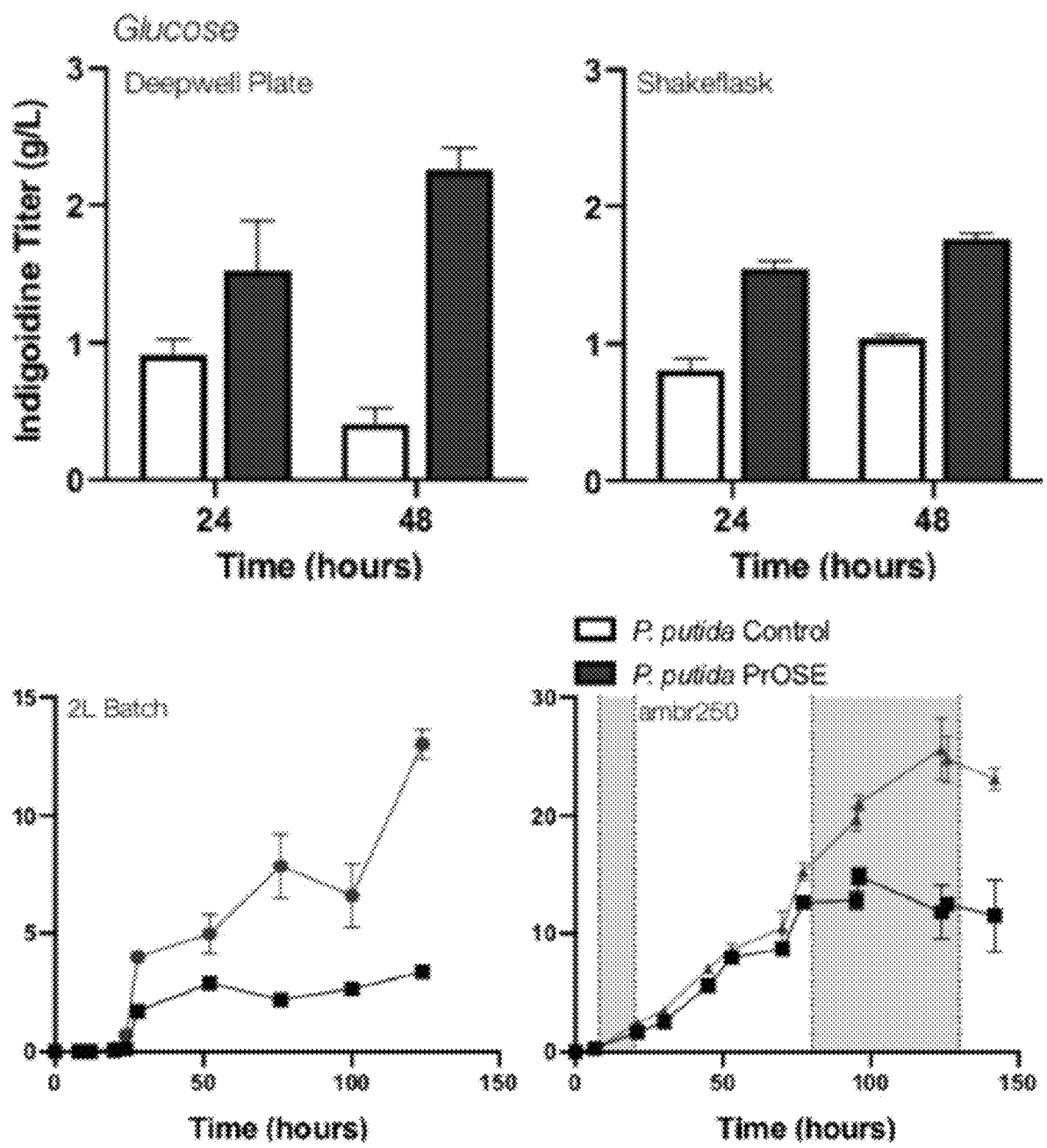
FIG. 3B. Analysis of *P. putida* PrOSE and a control strain for indigoidine production grown on M9 glucose. A fed-batch feeding regime is implemented in the ambr250 cultivation format. Glucose feeding is indicated by the gray shaded area. Control samples indicated with black outlined bars or black dots. The PrOSE strains are indicated with blue bars or blue dots.
Figure 3C:
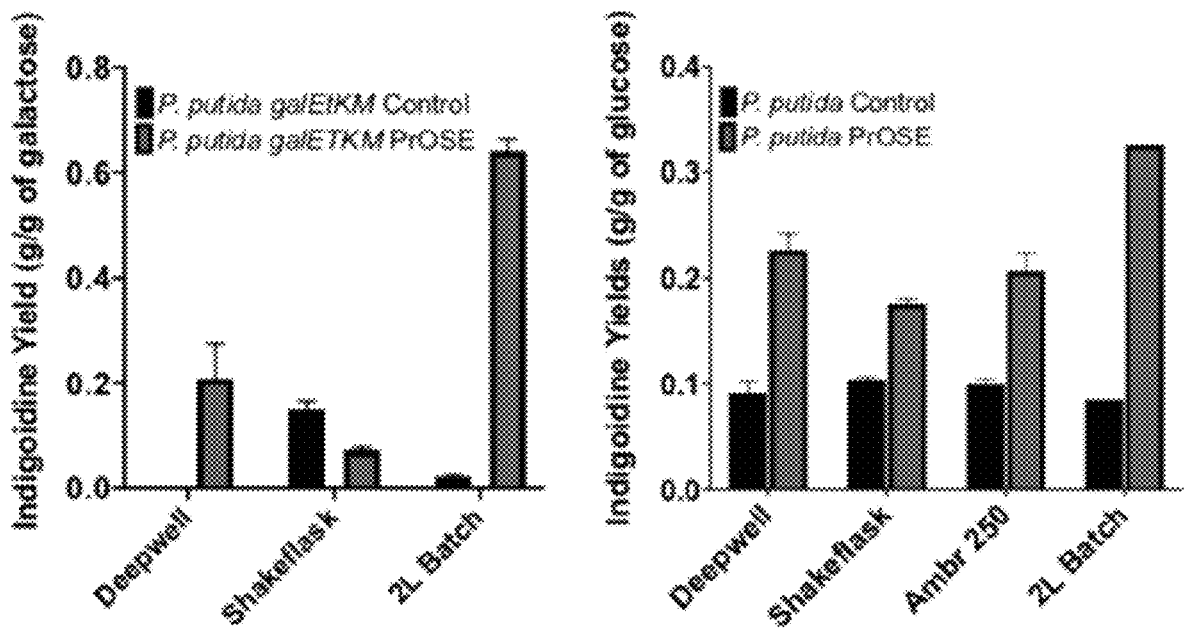
FIG. 3C. Analysis of indigoidine yield across cultivation formats for both glucose fed and galactose fed strains. Yield from the control strain is indicated with black bars, and the PrOSE strain is indicated with green bars.
Figure 4A:
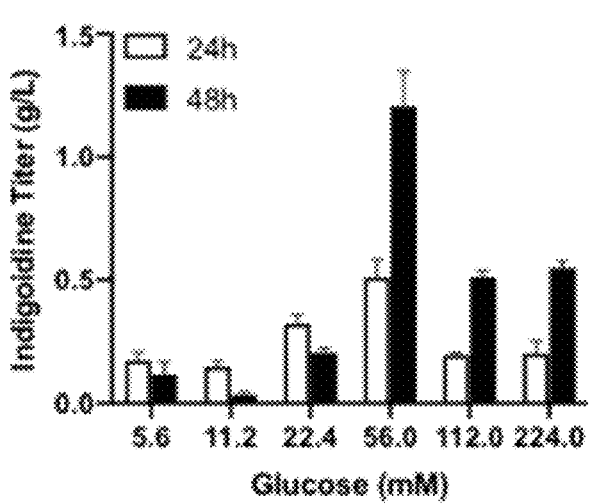
FIG. 4A. Optimizing carbon/nitrogen ratio yield only modest improvements to indigoidine production for glucose.
Figure 4B:
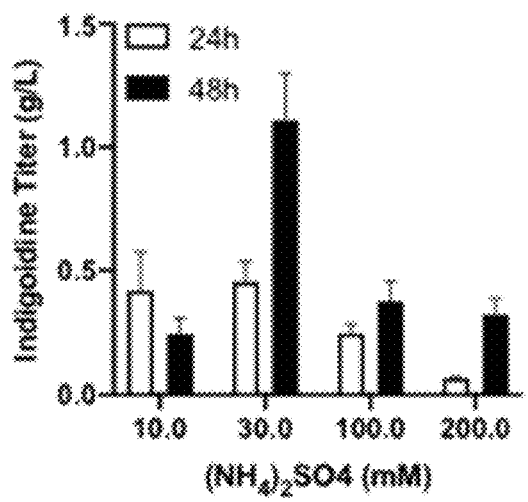
FIG. 4B. Optimizing carbon/nitrogen ratio yield only modest improvements to indigoidine production for $(NH_4)_2SO_2$.
Figure 4C:
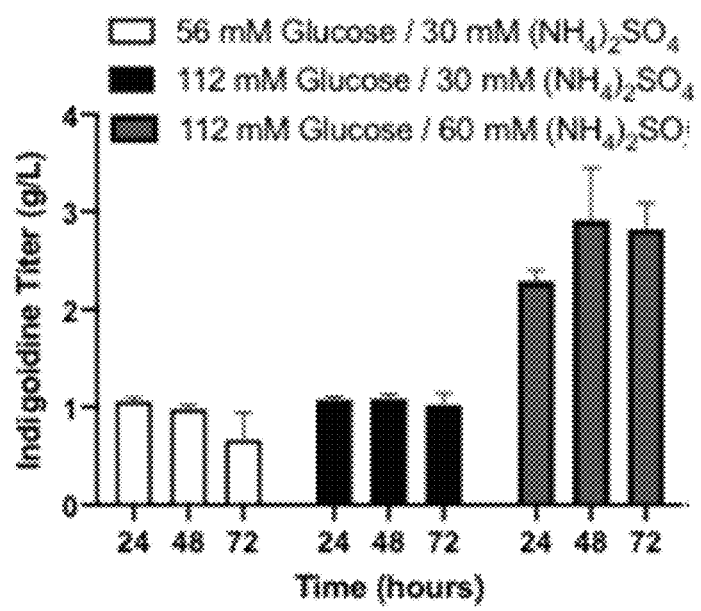
FIG. 4C. Optimizing carbon/nitrogen ratio yield only modest improvements to indigoidine production for glucose and $(NH_4)_2SO_2$.
Figure 4D:
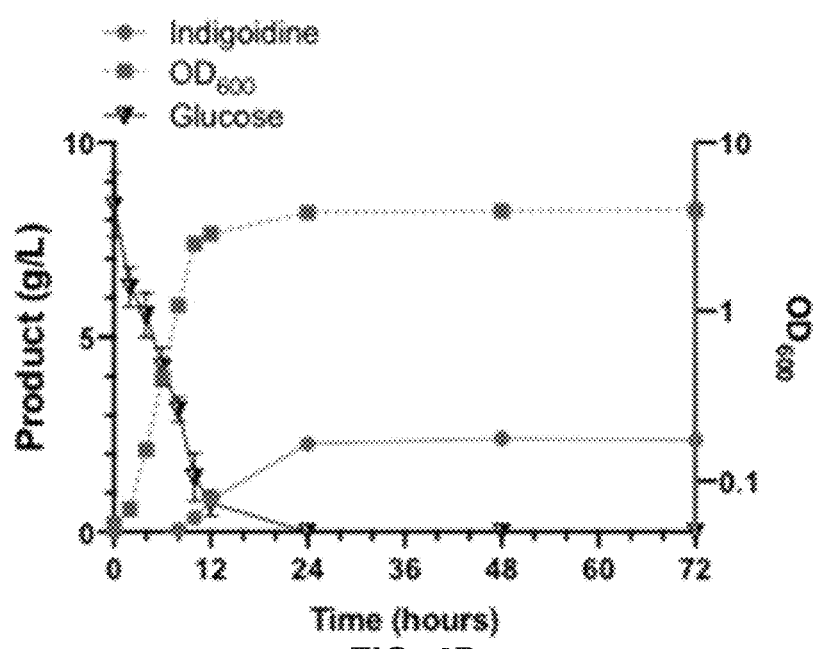
FIG. 4D. The basal production of Indigoidine in *P. putida* is 2.3 g/L indigoidine from 10 g/L glucose after 24 hours.

Building the PrOSE Strain:

To test the predictions from the metabolic modeling described above, the control and PrOSE P. putida system are built. First the heterologous production pathway is genomically integrated. The pathway for the indigoidine is comprised of sfp and bpsa. BpsA is a non-ribosomal peptide synthetase (NRPS) from Streptomyces lavendulae that catalyzes indigoidine formation from 2 molecules of glutamine in an ATP-dependent manner[20]. Activation of BpsA requires a post-translational pantetheinylation via a promiscuous Sfp from Bacillus subtilis. The genomically integrated production strain harboring a plasmid-borne dCpf1 and non-targeting gRNA serves as the control strain. The basal production of Indigoidine in P. putida is 2.3 g/L indigoidine from 10 g/L glucose after 24 hours (FIG. 4D). The bulk of production occurs in the stationary phase, approximately 12 hours after carbon depletion. To test the use of galactose, a galactose utilization strain is also engineered via genomic integration of a galETKM operon[18,19] and here production of indigoidine is negligible (FIGS. 4A to 4E). Optimizing carbon/nitrogen ratio yields only modest improvements to indigoidine production for both glucose and ammonium sulfate (FIGS. 1A to 4C).

Figure 4E:
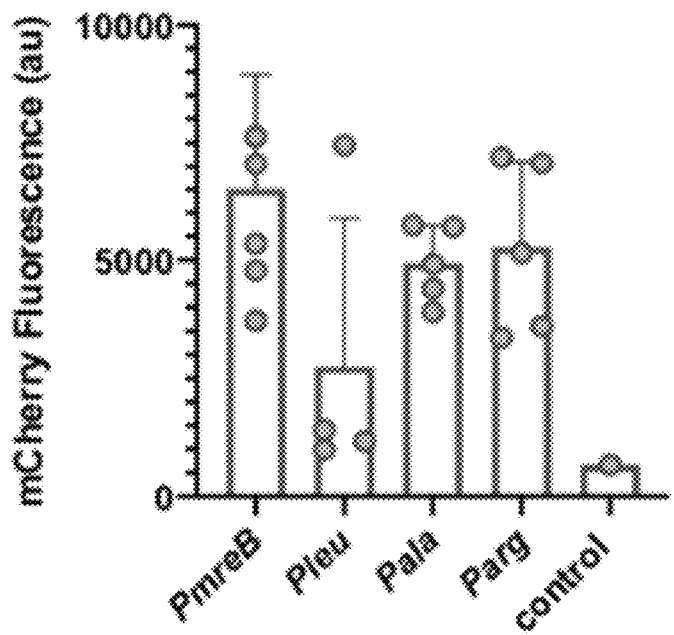
FIG. 4E. Minimal 100 bp promoter sequences from native tRNA ligases are sufficient to express mCherry fluorescent protein, confirming that heterologous mRNA transcripts for gRNAs would be generated under M9 glucose media.

Prior to construction of the PrOSE strain, the gene set is assessed to determine whether it contains any essential genes. The iJN1462 model has an incomplete list of essential genes; in addition genes as essential or dispensable are manually annotated using gene essentiality data generated from a barcoded fitness library (RB-TnSeq)[15]. Two genes are found to be essential. The remaining 14 genes are targeted for knockdown using a multiplex CRISPRi/dCpf1 targeting array. Based on the understanding of repetitive element instability[21,22] use of repeated DNA sequences is minimized to limit gRNA array loss. While other reports have indicated technical challenges constructing multiplex gRNA arrays[23], both native and synthetic repetitive arrays exist (including those of native CRISPR arrays)[24,25]. An endonuclease deficient class II CRISPR-Cas enzyme, Cpf1, is chosen over Cas9 as the Cpf1 crRNA is only 19 bp in size, compared to the corresponding crRNA (gRNA scaffold sequence) from Cas9, which is 76 bp[26]. Each gRNA is driven by a different *P. putida* tRNA ligase promoter/terminator pair and dCpf1 is placed under the control of the lacUV5 promoter. Minimal 100 bp promoter sequences from native tRNA ligases are sufficient to express mCherry fluorescent protein, confirming that heterologous mRNA transcripts for gRNAs would be generated (FIG. 4E).

Figure 2A:
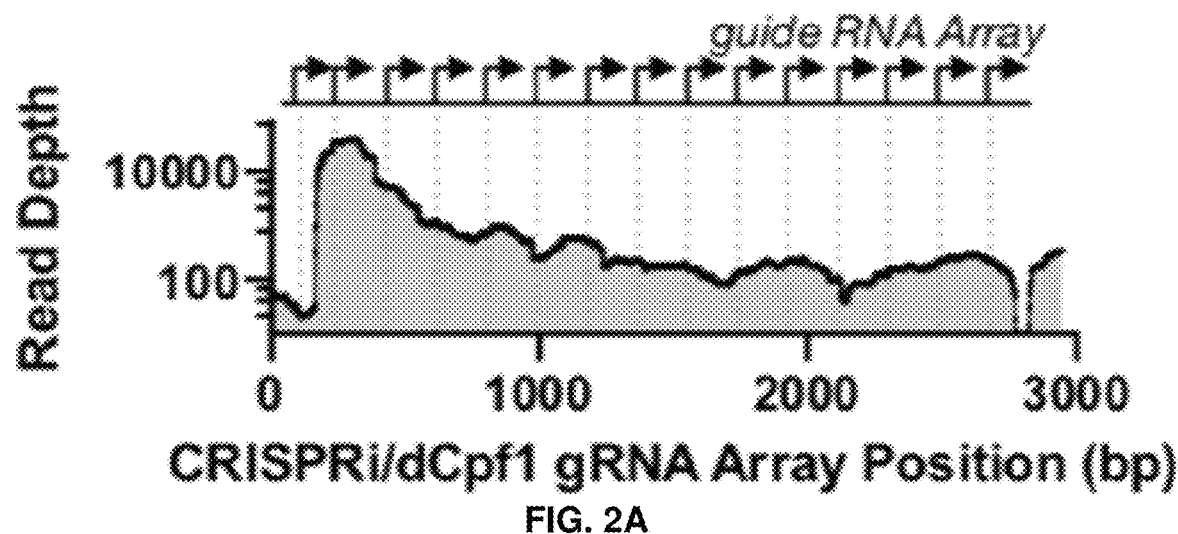
FIG. 2A: Characterization of the PrOSE strain via RNAseq and Proteomics. *P. putida* harboring a genomically integrated indigoidine expression cassette and either an empty vector (control strain) or a dCpf1/CRISPRi targeting array examined for gene knockdown efficiency.
Figure 2B:
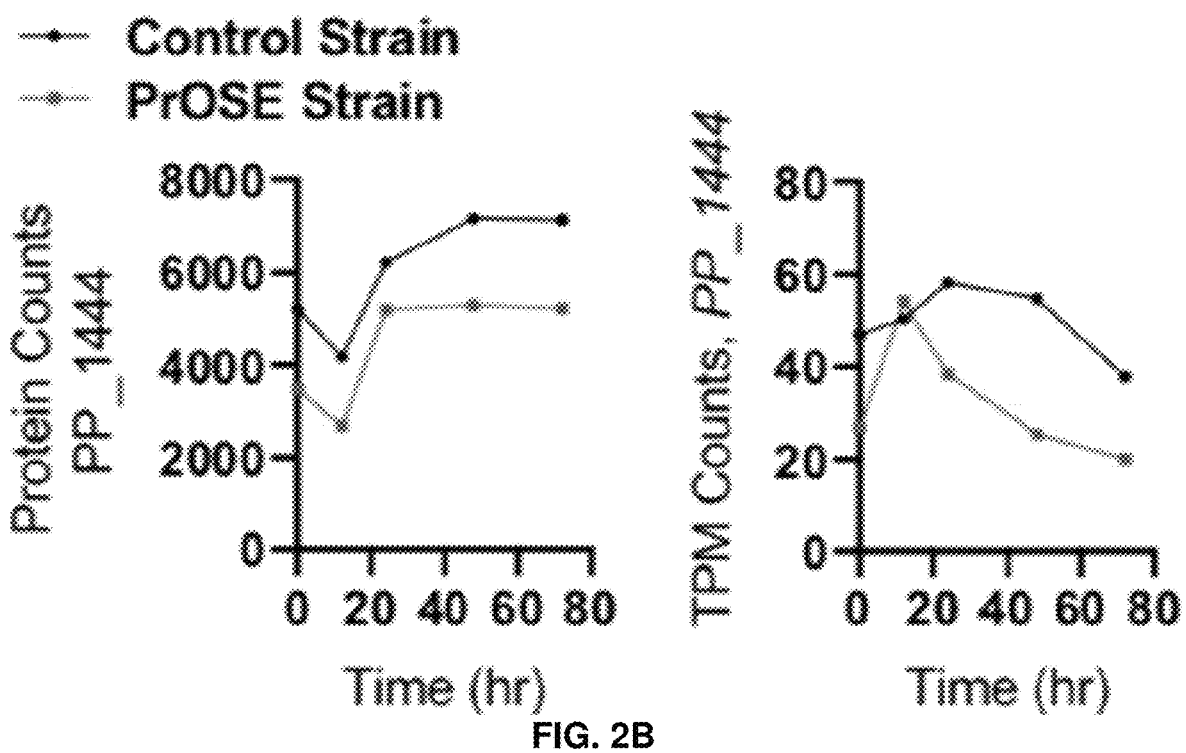
FIG. 2B. Knockdown efficiency of a representative gene locus targeted for inhibition over a 72 hour time course. RNA expression levels (right hand panel) are validated with high resolution targeted proteomic analysis (left hand panel).
Figure 2C:
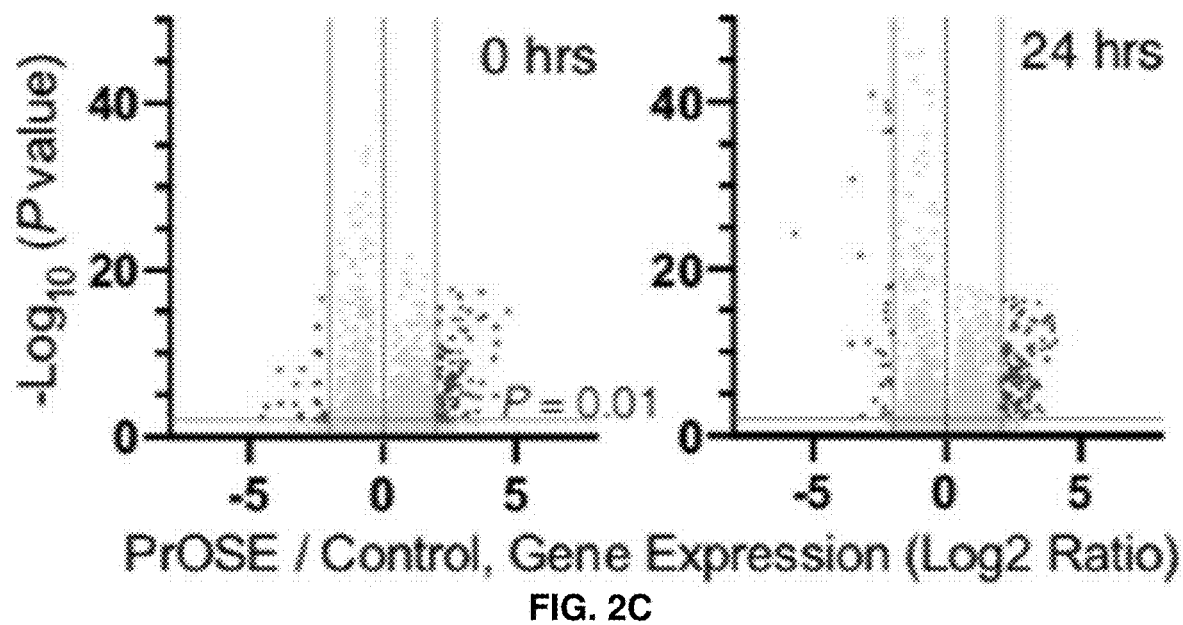
FIG. 2C. dCpf1/CRISPR interference causes global RNA expression level changes. Volcano plot of mRNA expression levels compared at t=0 h and t=24 h between PrOSE and control strains.
Figure 2D:
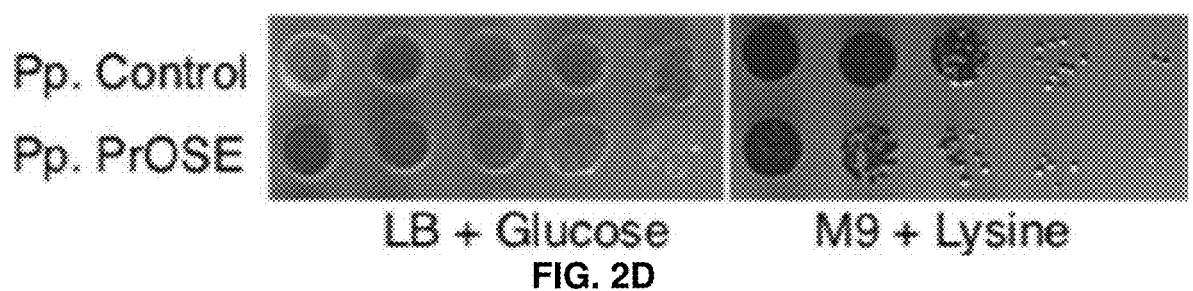
FIG. 2D. Validation of PrOSE substrate coupled predictions. PrOSE predicts that glucose/indigoidine rewiring blocks growth of engineered strains on lysine as a carbon source.

In a successful deployment of the multiplex CRISPRi/dCpf1 a decrease in mRNA expression levels (and protein abundance) is expected of the genes targeted with CRISPR interference. RNAseq analysis is used to examine the PrOSE strain, and compare normalized RNA expression levels between the control strain to a production strain carrying the glucose-PrOSE targeting plasmid (FIGS. 2A and 2B). RNA expression levels are sampled over the duration of a 72 hour time course. Expression of all 14 gRNAs are detected by this analysis. Expression of gRNAs is highest using the synthetic J23101 promoter but all native tRNA ligase promoters driving the remaining gRNAs in the array are functional. The multiplexed Cpf1 gRNAs in this array does not efficiently terminate with endogenous terminator sequences, and generated chimeric mRNAs are generated. Nonetheless, eight of the fourteen targeted gene loci exhibit decreased mRNA expression levels, but at best show a 50% decrease. Gene knockdown efficiency of the same samples is confirmed using high resolution proteomics and indicate a similar reduction of protein abundance (FIG. 2B). Despite the partial knockdown, growth assays show limited growth on lysine as carbon source, per the predictions from the FBA modeling (FIG. 2D).

Characterizing the ProSE Strain

A successful redirection metabolic flux to form glutamine, results in the PrOSE strain possessing several new quantifiable changes relative to the control. High TRY for the desired product is expected since more $Y_{P/S}$ glutamine should result in more indigoidine. The production of indigoidine would shift from stationary phase to exponential phase, as the cell must form glutamine/indigoidine to survive. And finally, these phenotypes should maintain fidelity across a range of growth modes and scales.

Whether indigoidine production is improved in the PrOSE relative to the control strains is tested in several laboratory cultivation formats. Production for both the native glucose carbon source as well as galactose are tested. The PrOSE and a control strain are cultivated with either 56 mM glucose or 56 mM galactose, as the same product obligatory targeted set would function on either carbon source. In a deep well plate format, it is observed that the PrOSE strain produce nearly three-fold more indigoidine than the control strain when fed glucose (FIGS. 3A to 3C). In a shake flask format, the PrOSE strain produces 30% more than the control strain. Finally, when cells are cultivated with galactose in the deep well format, the same PrOSE strain is able to produce indigoidine in contrast to the gal utilization control strain which only forms biomass.

In a batch-mode bioreactor, improved titers for indigoidine are observed when cells are cultivated with glucose as the carbon source. In this format, the PrOSE strain produces 12.5 g/L indigoidine from 60 g/L glucose. The control production strain, in contrast, produces 5 g/L, and production of the final molecule is still realized after glucose is exhausted from the media. When fed galactose, the PrOSE strain also shows improved titers under batch-mode conditions. The PrOSE strain successfully produces 25.6 g/L of indigoidine from 60 g/L galactose, while the control strain produces around 900 mg/L of indigoidine, a 28 fold improvement. Moving to an industrially relevant cultivation format did not impact final product titer, allowing further development of fed-batch cultivation methods with these strains.

Using a fed-batch cultivation regime realizes greater improvements in final product titer as well as production kinetics. After an initial high nutrient feed to increase biomass in the reactor, a reduced feed rate allows detection of indigoidine product formation during exponential phase growth. This observation fulfils the hypothesis which predicts that indigoidine formation must occur during exponential phase in order for the cell to survive. In terms of yield, the PrOSE strain shows consistently higher production than the control strain when cultivated with glucose, but is not as consistent when cultivated on galactose. Together all aspects of the phenotypes that are desirable for the PrOSE are found to be true.

DISCUSSION

The competition between biomass accumulation and production of the target compound is a well recognized challenge. This trade-off impacts both TRY and scalability. Approaches to address this tradeoff range from growth coupling[27] to growth decoupling[28].

Canonical examples of growth coupling include FBA-based methods such OptKnock[29], a well-used approach that identifies secondary pathways that reduce the pool of a key intermediate as means to increase flux to the target of interest. This strategy has been described as weak growth coupling[30] where growth still occurs even if the desired product is not being formed. Genomatica used weak growth coupling to improve 1,3 BDO production in *E. coli* to 18 g/L, but their strain engineering required a suite of additional refinements including adaptive lab evolution and bottleneck metabolite analysis[31] in order to implement at scale. Others have described growth coupling as the creation of a "driving force" such as ATP production or cofactor imbalance, and link the "driving force" to the desired production pathway[27, 32-34]. "Driving force" coupling is also pathway specific and requires additional strain engineering, such as for 1-butanol production in *E. coli* using NADH as the driving force[32] or media supplementation for butanone production that is linked to acetate assimilation in *E. coli*[27].

In contrast to the examples described above, PrOSE is an implementation of strong growth coupling. It relies on EMA based methods that have been shown at genome scale level[13,35,36] but often suggests a large number of enzymatic reactions for elimination. FBA is used to validate the optimal cMCS and removes essential genes from targeted gene sets using-omics data to determine which genes should be targeted for CRISPRi. This work is the first experimental implementation of a genome-scale strong growth coupling solution set. Reliability in scaling is a necessary part of strain engineering that also remains unexplored in most cases. When pursued it often takes years. A successful implementation of PrOSE allows one to achieve in one cycle of strain engineering not only a very high TRY but also due to the inherent obligatory product formation, the production parameters are consistently maintained from batch to fed-batch and from microtiter plates to 2 L bioreactors.

In the context of TRY improvement alone, indigoidine itself is an example of a heterologous product that has been demonstrated at high titers[37-39]. The production of indigoidine is high in the oleaginous yeast *Rhodosporidium toruloides* but remains low in the model yeast *S. cerevisiae*, despite similar optimization of cultivation parameters. This comparison represents an empirical example of the innate metabolic potential of a given host, and is consistent with our calculated max theoretical yields for indigoidine (Table 3). Genome scale metabolic models can accurately predict how microbial hosts could be advantageous for the production of a given metabolite. For indigoidine, the max $Y_{P/S}$ from glucose in *P. putida* is 0.54 and is comparable to that for *R. toruloides*, while *E. coli* and *S. cerevisiae* are much lower. It is likely that every molecule will be different. Thus selecting the best host/final product pair is a crucial aspect of developing the ideal production platform.

While this implementation of PrOSE is successful, several caveats of this approach are not addressed in this study. For indigoidine production in *P. putida*, the 90% maximum yield that is theoretically possible is not reached (whereas industrial yeast ethanol production is near 90% MTY). It is speculated that this is due to the incomplete knockdown on the gene set. With a better understanding of the terminator sequence efficiency (as observed in *P. putida* and *E. coli*[23]) more efficient CRISPR mediated gene knockdown may be achieved. Additional MFA analysis from 13C glucose or 13C galactose using these strains could also refine the genome scale models, enabling more accurate metabolic flux modeling when these engineered strains are grown with these carbon sources. PrOSE also relies on the availability of a high quality genome scale metabolic models, and product obligatory growth is calculated using a single carbon source. Thus currently, PrOSE cannot be used for certain mixed carbon streams, such as glucose and xylose, as our calculations for glucose-PrOSE inactivates the pentose phosphate pathway. Similarly, there are metabolites that cannot be made obligatory for growth[13]. Alternative strategies for final products derived from this class of metabolites would need to be explored. Products or intermediates that may be toxic are not considered. As final processes also use renewable carbon sources that may contain inhibitory byproducts, microbial hosts will require some degree of tolerance engineering[40] to unlock its potential. Addressing these aspects will further boost the usefulness of PrOSE.

This approach is a significant step forward in realizing the full potential of microbial processes. Part of the appeal of genome scale models is that their genetic solutions are scale-agnostic; the predicted metabolic rewiring should apply even in the largest bioreactor formats. PrOSE is the first implementation of theoretical predictions for product obligatory metabolite production and is realized by multiplex CRISPR interference. By making the final desired product obligatory for growth, one is able to mimic native obligatory product formations such as ethanol production in budding yeast that have been so successful. Further, there are apparently no other examples in which production of a non-native molecule is deliberately shifted from stationary phase to exponential phase as a result of strain engineering. This holistic approach represents a new paradigm for the evaluation and optimization of microbial host/final product pairs.

The optimization of final product titer, rate, and yield during scale-up is arguably the most critical step required to support the field of biotechnology; it is also the most laborious and time consuming. For example, the heterologous production of isopentenol in *E. coli* has been improved from trace concentrations to >2 g/L over a decade of experimental work[41,42]. PrOSE provides a powerful new approach to significantly reduce the time taken to achieve these high production parameters, and inherently designs a strain that maintains its production parameters across scales.

MATERIALS AND METHODS

Computation of Constrained Minimal Cut Sets (cMCS)

*Pseudomonas putida* KT2440 genome scale metabolic model (GSM) iJN1462[11] is used. The ATP maintenance demand and glucose uptake are 0.97 mmol ATP/gDW/h and 6.3 mmol glucose/gDW/h respectively. Constrained minimal cut sets (cMCS) are calculated according to the algorithm as previously described[13]. Excretion of byproducts is initially set to zero, except for the reported overflow metabolites for secreted products specific to *P. putida* (gluconate, 2 ketogluconate, 3 oxoadipate, catechol, lactate, methanol, $CO_2$, and acetate). Additional inputs including minimum demanded product yield (% of the maximum product yield) and minimum demanded biomass yield are also specified in order to constrain the desired design space. Knockouts of export reactions and spontaneous reactions are not allowed. The algorithm computes for all minimal combinations of reaction knockouts blocking all undesired flux distributions and maintaining at least one of the desired metabolic flux distributions. With the specifications used herein each calculated knockout strategy (cMCS) ensures that growth is not feasible without biosynthesis of glutamine. (Growth production locking/strong growth coupling/Product obligatory growth). All cMCS calculations are done using API functions of CellNetAnalyzer[43] on MATLAB 2017b platform using CPLEX 12.8 as the MILP solver. Once all the cMCS are enumerated, the PrOSE workflow (FIG. 1A) is used to find the best engineering strategy to carry forward.

Constraint Based Methods to Confirm the cMCS iJN1462 is extended to account for indigoidine biosynthesis pathway and checked for strong growth coupling to confirm the chosen engineering strategy for experimental implementation. Flux Balance Analysis (FBA) is used to calculate the maximum theoretical yield (MTY) from reaction stoichiometry and redox balance and for single gene deletion analysis. Flux variability analysis (FVA) along with FBA is used to check for minimum and maximum glutamine or indigoidine flux under the identified cMCS strategy to confirm product obligatory growth. COBRA Toolbox v.3.0[44] in MATLAB R2017b is used for FBA and FVA simulations with the GLPK (website for: gnu.org/software/glpk), an open-source linear optimization solver.

Chemicals, Media and Culture Conditions

All chemicals and reagents are purchased from Sigma-Aldrich (St. Louis, Mo.) unless mentioned otherwise. When cells are cultivated in a microtiter dish format, plates are sealed with a gas-permeable film (Sigma-Aldrich, St. Louis, Mo.). Tryptone and yeast extract are purchased from BD Biosciences (Franklin Lakes, N.J.). Engineered strains are grown on M9 Minimal Media as described previously[45] with slight modifications. Carbon sources (glucose, p-coumarate or galactose) are used at 10 g/L and $(NH_4)_2SO_4$ is used at 2 g/L.

Strains and Strain Construction

*Pseudomonas putida* KT2440 is used as the host for strain engineering. Electroporation with the respective plasmid is performed using BIORAD MicroPulser preprogrammed EC2 setting (0.2 cm cuvettes with 100 uL cells, ~5 msec pulse and 2.5 kV). Transformed cells are allowed to recover at 25 C for around 2.5 hours followed by plating onto selective media (containing respective antibiotics) and overnight incubation. Positive clones are confirmed for the genotype by colony PCR using Q5 Polymerase enzyme (NEB, Ipswitch, Mass.). The dCpf1/CRISPRi system[26] is adapted for use in *P. putida* by subcloning dCpf1 into a pBBR1 backbone and placed under the LacUV5 promoter. The synthetic gRNA array is constructed using gene synthesis techniques (Genscript, Piscataway, N.J.) and cloned into the dCpf1/CRISPRi backbone using isothermal DNA assembly. All plasmid constructs are verified with Sanger sequencing before transformation into *Pseudomonas putida*.

Analytics/Sugar Quantification—HPLC

Glucose and organic acids from cell cultures are measured by an 1100 Series HPLC system equipped with a 1200 Series refractive index detector (RID) (Agilent) and Aminex HPX-87H ion-exclusion column (300 mm length, 7.8 mm internal diameter; Bio-Rad Laboratories, Inc., Hercules, Calif.). Three hundred-microliter aliquots of cell cultures are removed at various time points during production and filtered through a spin-cartridge with a 0.45-μm nylon membrane, and 10 μL of the filtrate is eluted through the column at 50° C. with 4 mM sulfuric acid at a flow rate of 600 μL/min for 30 min. Metabolites are quantified by using external standard calibration with authentic standards.

Indigoidine Quantification

Figure 5:
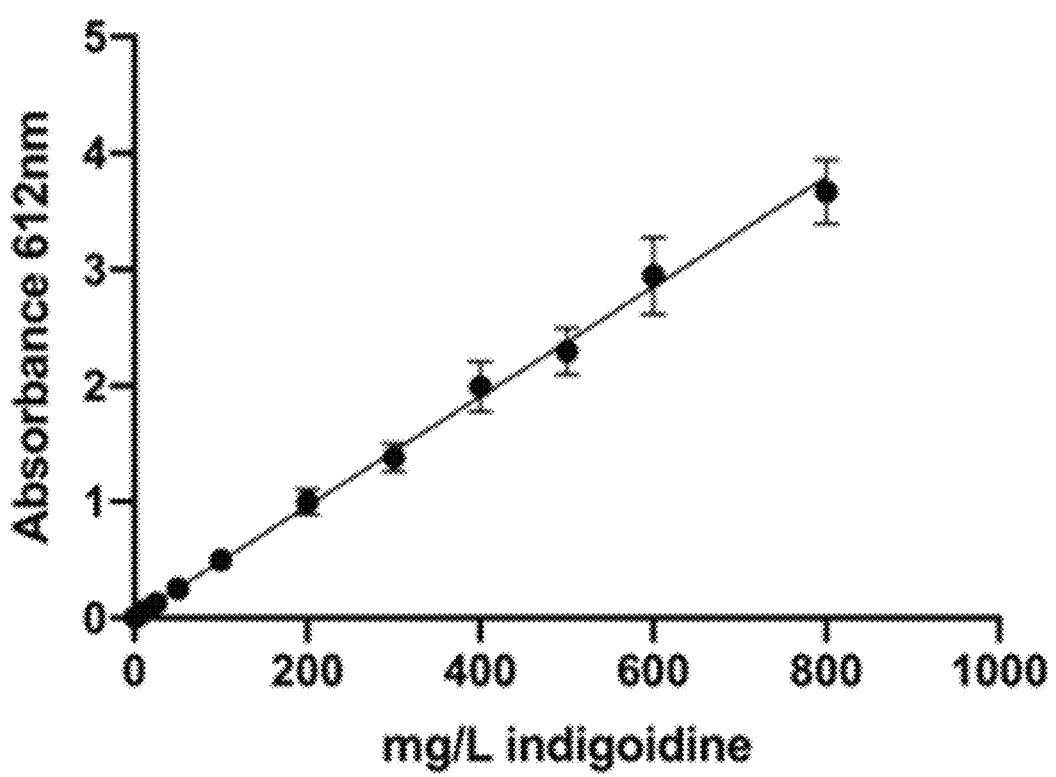
FIG. 5. Standard curve used for indigoidine quantification. R squared is 0.9843. Equation: Y=0.004723*X+0.01645. Working equation: Y=211.729833X−3.48295575. Y(mg/L) Indigoidine=211.729833 $A_{612}$−3.48295575. y(g/L) Indigoidine=0.212 $A_{612}$−0.0035.
Figure 6:
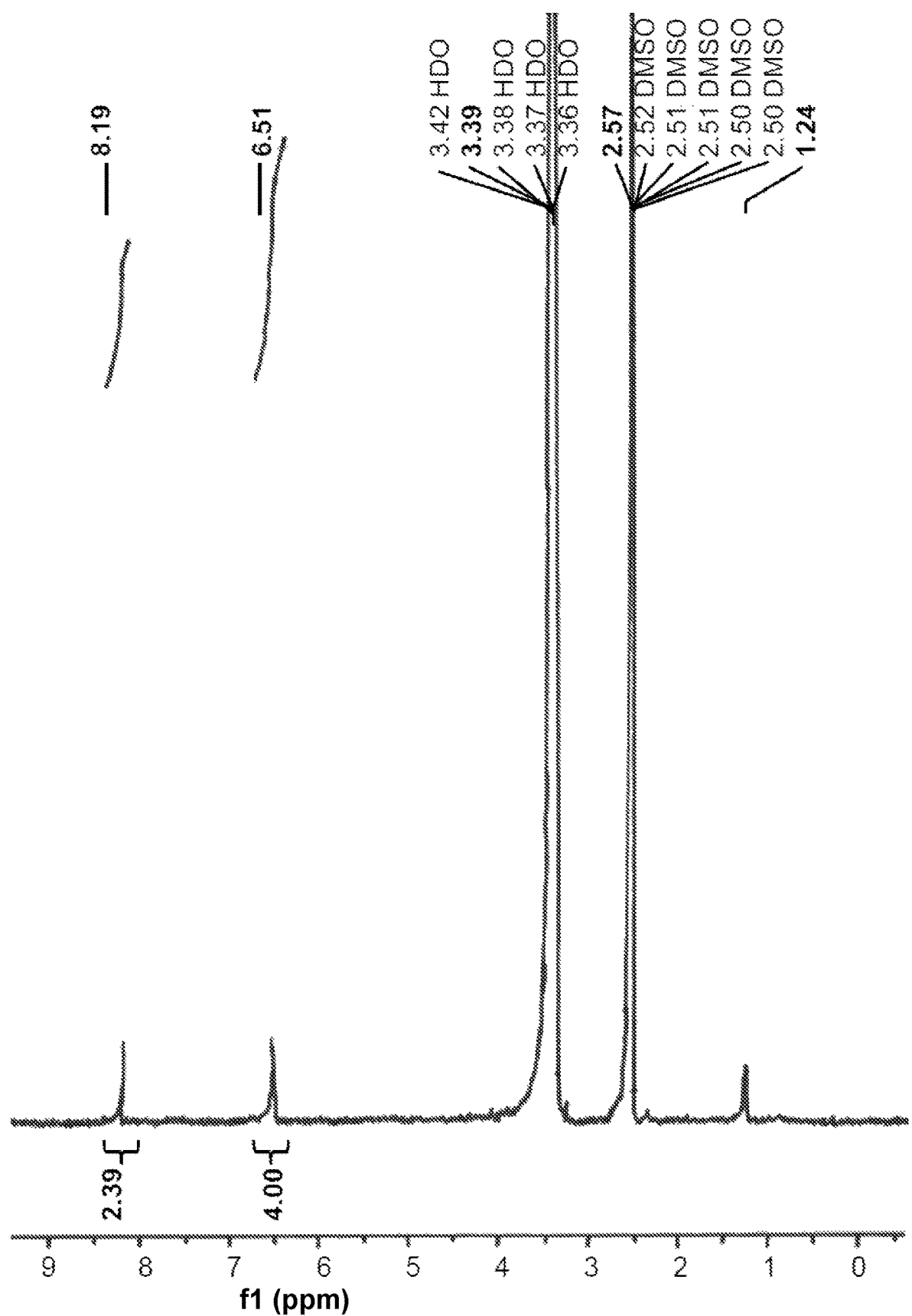
FIG. 6. NMR Spectra.

Briefly, 100 uL of cells is pelleted by centrifugation at 15000 rpm for 2 min. The supernatant is discarded and 500 uL DMSO is added to the pellet. The solution is vortexed vigorously for 30 s to dissolve Indigoidine. After centrifugation at 15000 rpm for 2 min, 100 μL of DMSO extracted indigoidine is added to 96-well flat-bottomed microplates. Indigoidine is quantified by measuring the optical density at 612 nm wavelength ($OD_{612}$) using a microplate reader (Molecular Devices Spectramax M2E) preheated to 25° C. and applying standard curve generated from indigoidine purified from *P. putida* (FIG. 5). Equation of Y (g/L of Indigoidine)=$0.212*A_{612}-0.0035$. The purity of extracted indigoidine from both *E. coli* and *P. putida* are cross-validated by NMR (method) (FIG. 6).

RNAseq and Data Analyses

Total RNA is prepared following standard laboratory protocols[46] for Trizol RNA extraction with several modifications. RNA from trizol treated lysates are bound to a silica column (Direct-zol RNA MiniPrep Plus Kit, Zymo Research, Irvine, Calif.) and its integrity confirmed using a Bioanalyzer RNA 6000 Nano assay (Agilent Technologies, Santa Clara, Calif.). Preparation of total RNA for RNAseq analysis is conducted at the DOE Joint Genome Institute on an Illumina MiSeq with 300 bp paired end reads. Reads are assembled to the reference genome using BowTie with the following parameters. Reported gene expression values are the total normalized transcripts per million (TPM).

Targeted Proteomics

Targeted proteomics is conducted as previously described[47].

Cultivation at Different Scales

Cultures from glycerol stocks are struck to single colonies on LB agar media with the appropriate antibiotic as necessary. Single colonies are used to inoculate overnight cultures in LB with the appropriate antibiotic. Saturated overnight LB cultures are then back-diluted 1/100× into M9 minimal media with the appropriate carbon source as indicated. Cultures are back-diluted and adapted twice to ensure robust cell growth before heterologous pathway induction. All cultures are incubated with shaking at 200 rpm and 30° C. To prepare cells for pathway induction, M9 adapted cultures are back-diluted to a starting OD600 of 0.1, at which point IPTG and arabinose are added as appropriate. Production cultures are grown in 24 well deep well plates inoculated into a 200 uL culture volume and incubated InFors Multitron HT Double Stack Incubator Shaker set to 999 rpm linear shaker, and 70% humidity. For shake flask experiments, 60 mL cultures are grown in 250 mL unbaffled Erlenmeyer shake flask and incubated at 200 rpm with orbital shaking. For all experiments, the indigoidine pathway is induced with 0.3% w/v L-arabinose, and dCpf1 mediated gene repression is induced with 500 μM IPTG. Indigoidine production titers are also analyzed in Lysogeny-Broth (LB) containing 10 g/L tryptone, 5 g/L yeast extract, and 5 g/L NaCl.

Fed-Batch Experiments at 2 L Bioreactor Scale

Fed-batch experiments are performed at 2 L scale using a Sartorius BIOSTAT B® fermentation controller, fitted with two Rushton impellers fixed at 800 rpm. Initial reactor volume of 1 L M9 Minimal Media (10 g/L Glucose, 0.3% w/v L-arabinose, 30 mM NH4+), and 50 mL overnight pre-culture in the same media. Cultivation temperature held at 30° C. Bioreactor processes are maintained to pH 7 using 10 M NaOH.

Ambr Method: 250 mL ambr250™ Bioreactor Cultivations

Bioreactor experiments are carried out in a 12-way ambr250 bioreactor system (Sartorius Stedim Biotech GmbH, Goettingen, Germany) equipped with 250 mL single-use, disposable bioreactors (Microbial vessel type). The vessels are filled with 150 mL M9 minimal salt media for experiments with glucose as carbon source. Temperature is maintained at 30° C. throughout the fermentation process and agitation is set constant to 1300 RPM. Airflow is set constant to 0.5 VVM based on respective initial working volumes and pH is maintained at 7 using 4 N NaOH. Reactors are inoculated manually with pipettes with 5 mL of cell suspension grown under seed culture. After an initial batch phase of 12 hours, cultures with glucose as carbon source are fed with a concentrated glucose feed solution (600 g/L glucose; Feed solution A) using two separate feed strategies: continuous feeding for one strain and pulsed feeding for another strain. For the continuous feed, the initial feed delivery is maintained at 5 g $_{glc}$/Lh or 1.292 mL/h. Pulsed feed is administered every two hours in the form of boluses restoring glucose concentrations to 10 g/L (feed parameters: 3.1 min @ 50 mL/h). After observing glucose accumulation, feed addition is paused for both conditions. Feed is resumed when glucose levels dropped below 10 g/L at reduced feed rates: 1 g $_{glc}$/Lh or 0.258 mL/h (continuous feed) and 3.23 g $_{glc}$/L or 1 min @ 50 mL/h (pulse feed). Similarly, during the fed-batch stage, recurring carbon exhaustion events are observed by DO signal spikes that triggered feed addition (Feeding parameters: ΔDO=15%, 10 min @ 33 mL/h). Samples are taken once every day (2 mL) and stored at −20° C. The ambr250 runtime software is used to execute all process steps unless stated otherwise.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A genetically modified *Pseudomonas* host cell capable of producing indigoidine, wherein the host cell comprises a *Bacillus subtilis* 4'-phosphopantetheinyl transferase (Sfp) and a non-ribosomal peptide synthetase (NRPS) comprising an amino acid sequence that is at least 90% identical to the amino acid sequence of SEQ ID NO:1, and the amino acid sequence SRRLEREV (SEQ ID NO:3), or SRRLEREVAQESSRLVRLHAE (SEQ ID NO:4), at the position corresponding to 1005 to 1012, or 1005 to 1025, of SEQ ID NO:1, respectively, wherein the NRPS converts glutamine to indigoidine, and the *Pseudomonas* host cell is reduced in its expression of the following enzymes: Glucose dehydrogenase (ubiquinone 8 as acceptor, periplasm); Phosphoenolpyruvate synthase; Malate dehydrogenase; Malate dehydrogenase (ubiquinone 8 as acceptor); Malic enzyme NADP (malate dehydrogenase (oxaloacetate-decarboxylating)(NADP+)); and Transaldolase.

2. The genetically modified *Pseudomonas* host cell of claim 1 wherein the *Pseudomonas* cell is a *Pseudomonas putida*.

3. The genetically modified *Pseudomonas* host cell of claim 1, wherein the NRPS is a bacterial NRPS.

4. The genetically modified *Pseudomonas* host cell of claim 3, wherein the NRPS is a *Streptomyces lavendulae* NRPS (BpsA).

5. The genetically modified *Pseudomonas* host cell of claim 1, wherein the NRPS comprises a conserved domain, such as the amino acid sequence APRTETEKEI AEVWAKSLRR ESVSVQDDFF ESGGNSLIAV GLIRELNSRL GVSLPLQSVL ESPTVEKLSR RLEREV (SEQ ID NO:2), at the position corresponding to 937 to 1012 of SEQ ID NO:1.

6. A method for a genetically modified *Pseudomonas* host cell producing indigoidine, comprising (a) providing the genetically modified *Pseudomonas* host cell of claim 1, (b) culturing or growing the host cell in a suitable culture or medium such that indigoidine is produced, and (c) optionally extracting or separating the indigoidine from the rest of the culture or medium, and/or host cell.

7. The method of claim 6, wherein the providing step (a) comprises introducing a nucleic acid encoding the NRPS operatively linked to a promoter capable of expressing the NRPS in the host cell into the host cell.

8. The method of claim 6, wherein the culturing or growing step (b) comprises the host cell growing by respiratory cell growth.

9. The method of claim 6, wherein the culturing or growing step (b) takes place in a batch process or a fed-batch process, such as a high-gravity fed-batch process.

10. The method of claim 6, wherein the culture or medium comprises hydrolysates derived or obtained from a biomass, such as a lignocellulosic biomass.

11. The method of claim 6, wherein the culture or medium comprises one or more carbon sources, such as a sugar, such as glucose or galactose, or glycerol, or a mixture thereof.

12. The method of claim 11, wherein the carbon source is fermentable; in some embodiments, the carbon source is non-fermentable.

13. The method of claim 6, wherein the culture or medium comprises urea as a nitrogen course.

14. The method of claim 6, comprising introducing a nucleic acid encoding the NRPS operatively linked to a promoter capable of expressing the NRPS in the host cell into the host cell.

15. The genetically modified *Pseudomonas* host cell of claim 1, wherein the NRPS comprises an amino acid sequence that is at least 95% identical to the amino acid sequence of SEQ ID NO:1.

16. The genetically modified *Pseudomonas* host cell of claim 15, wherein the NRPS comprises an amino acid sequence that is at least 99% identical to the amino acid sequence of SEQ ID NO:1.

17. The genetically modified *Pseudomonas* host cell of claim 16, wherein the NRPS comprises the amino acid sequence of SEQ ID NO:1.

18. The genetically modified *Pseudomonas* host cell of claim 1, wherein the *Pseudomonas* host cell is further reduced in its expression of one or more of the following enzymes or enzymes catalyzing the indicated reactions: N acetylornithine deacetylase; Ornithine Decarboxylase; Proline dehydrogenase; Poly 3 hydroxyalkanoate polymerase 3 Hydroxybutanoyl CoA (poly(3-hydroxyalkanoate) polymerase 1); 1,6 anhydrous N Acetylmuramate kinase; D lactate transport via proton symport periplasm; Carboxylic acid dissociation; and HCO3 equilibration reaction.

* * * * *